United States Patent
Valton et al.

(10) Patent No.: US 10,894,093 B2
(45) Date of Patent: Jan. 19, 2021

(54) METHOD OF ENGINEERING DRUG-SPECIFIC HYPERSENSITIVE T-CELLS FOR IMMUNOTHERAPY BY GENE INACTIVATION

(71) Applicant: CELLECTIS, Paris (FR)

(72) Inventors: Julien Valton, New York, NY (US); Veronique Zennou, Jersey City, NJ (US); Philippe Duchateau, Draveil (FR); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 57 days.

(21) Appl. No.: 16/092,417

(22) PCT Filed: Apr. 13, 2017

(86) PCT No.: PCT/EP2017/058922
§ 371 (c)(1),
(2) Date: Oct. 9, 2018

(87) PCT Pub. No.: WO2017/178585
PCT Pub. Date: Oct. 19, 2017

(65) Prior Publication Data
US 2019/0151478 A1    May 23, 2019

(30) Foreign Application Priority Data

Apr. 15, 2016 (DK) ................................ 2016 70232

(51) Int. Cl.
| | |
|---|---|
| *C12N 5/0783* | (2010.01) |
| *C12N 15/113* | (2010.01) |
| *A61P 31/00* | (2006.01) |
| *A61K 48/00* | (2006.01) |
| *A61K 35/17* | (2015.01) |
| *C07K 14/725* | (2006.01) |
| *A61P 35/00* | (2006.01) |

(52) U.S. Cl.
CPC .......... *A61K 48/0091* (2013.01); *A61K 35/17* (2013.01); *A61K 48/0008* (2013.01); *A61K 48/0058* (2013.01); *A61K 48/0066* (2013.01); *A61P 31/00* (2018.01); *A61P 35/00* (2018.01); *C07K 14/7051* (2013.01); *C12N 5/0636* (2013.01); *C12N 15/113* (2013.01); *C12N 2310/20* (2017.05); *C12N 2510/00* (2013.01)

(58) Field of Classification Search
None
See application file for complete search history.

(56) References Cited

U.S. PATENT DOCUMENTS

2013/0316391 A1* 11/2013 Bourner ............... G01N 33/502
                                                                  435/29
2016/0017048 A1    1/2016 Dotti et al.

FOREIGN PATENT DOCUMENTS

| WO | 99/05299 A1 | 2/1999 | |
| WO | 01/16331 A1 | 3/2001 | |
| WO | 2005/056749 A2 | 6/2005 | |
| WO | 2012/092379 A2 | 7/2012 | |
| WO | WO-2014191128 A1 * | 12/2014 | ............ C12N 15/85 |
| WO | 2015/075195 A1 | 5/2015 | |
| WO | 2015/140268 A1 | 9/2015 | |
| WO | 2017/178586 A1 | 10/2017 | |

OTHER PUBLICATIONS

S-E Kim et al: "[gama]-Glutamyl hydrolase modulation and folate influence chemosensitivity of cancer cells to 5-fluorouracil and methotrexate", British Journal of Cancer, 109, No. 8, Sep. 17, 2013 (Sep. 17, 2013), pp. 2175-2188.

S. Doublier et al: RhoA Silencing Reverts the Resistance to Doxorubicin in Human Colon Cancer Cells, Molecular Cancer Research, vol. 6, No. 10, Oct. 1, 2008 (Oct. 1, 2008), pp. 1607-1620.

Yuan Xiao Zhu et al: "RNAi screen of the druggable genome identities modulators of proteasome inhibitor sensitivity in myeloma including CDK5", Blood, Feb. 2, 2011 (Feb. 2, 2011), 3847-57.

Attila A. Seyhan et al: "A genome-wide RNAi screen identifies novel targets of neratinib sensitivity leading to neratinib and paclitaxel combination drug treatments", Molecular Biosystems, vol. 7, No. 6, Jul. 1, 2011 (Jul. 1, 2011), 1974-89.

Lihua E. Budde et al: "Combining a CD20 Chimeric Antigen Receptor and an Inducible Caspase 9 Suicide Switch to Improve the Efficacy and Safety of T Cell Adoptive Immunotherapy for Lymphoma", PLOS One, vol. 8, No. 12, Dec. 17, 2013 (Dec. 17, 2013), p. e82742.

V Hoyos et al: Engineering CD19-specific T lymphocytes with interleukin-15 and a suicide gene to enhance their anti-lymphoma/leukemia effects and safety, Leukemia, vol. 24, No. 6, Apr. 29, 2010 (Apr. 29, 2010), pp. 1160-1170.

(Continued)

*Primary Examiner* — Daniel C Gamett
(74) *Attorney, Agent, or Firm* — Arrigo, Lee, Guttman & Mouta-Bellum LLP

(57) ABSTRACT

The present invention relates to therapeutic cells for immunotherapy to treat patients with cancer. In particular, the inventors develop a method of engineering drug-specific hypersensitive T-cell, which can be depleted in vivo by the administration of said specific drug in case of occurrence of a serious adverse even. The invention opens the way to standard and affordable adoptive immunotherapy strategies for treating cancer.

21 Claims, 1 Drawing Sheet

Specification includes a Sequence Listing.

(56) References Cited

OTHER PUBLICATIONS

Marin V et al: "Comparison of different suicide-gene strategies for the safety improvement of genetically manipulated T cells", Human Gene Therapy Methods, vol. 23, No. 6, Nov. 27, 2012 (Nov. 27, 2012), pp. 376-386.

Anliker Brigitte et al: "Therapeutic approaches using genetically modified cells", Bundesgesundheitsblatt—Gesundheitsforschung—Gesundheitsschutz, Springer Berlin Heidelberg, Berlin/Heidelberg, vol. 58, No. 11, Sep. 8, 2015 (Sep. 8, 2015), pp. 1274-1280.

Amara Ikrame et al: "Mesenchymal stem cells as cellular vehicles for prodrug gene therapy against tumors", Biochimie, Masson, Paris, FR, vol. 105, Jun. 27, 2014 (Jun. 27, 2014), pp. 4-11.

Walid Touati et al: "A Suicide Gene Therapy Combining the Improvement of Cyclophosphamide Tumor Cytotoxicity and the Development of an Anti-Tumor Immune Response", Current Gene Therapy, vol. 14, No. 3, Aug. 8, 2014 (Aug. 8, 2014), pp. 236-246.

European Patent Office, International Search Report for PCT/EP2017/058923 dated Sep. 18, 2017.

\* cited by examiner

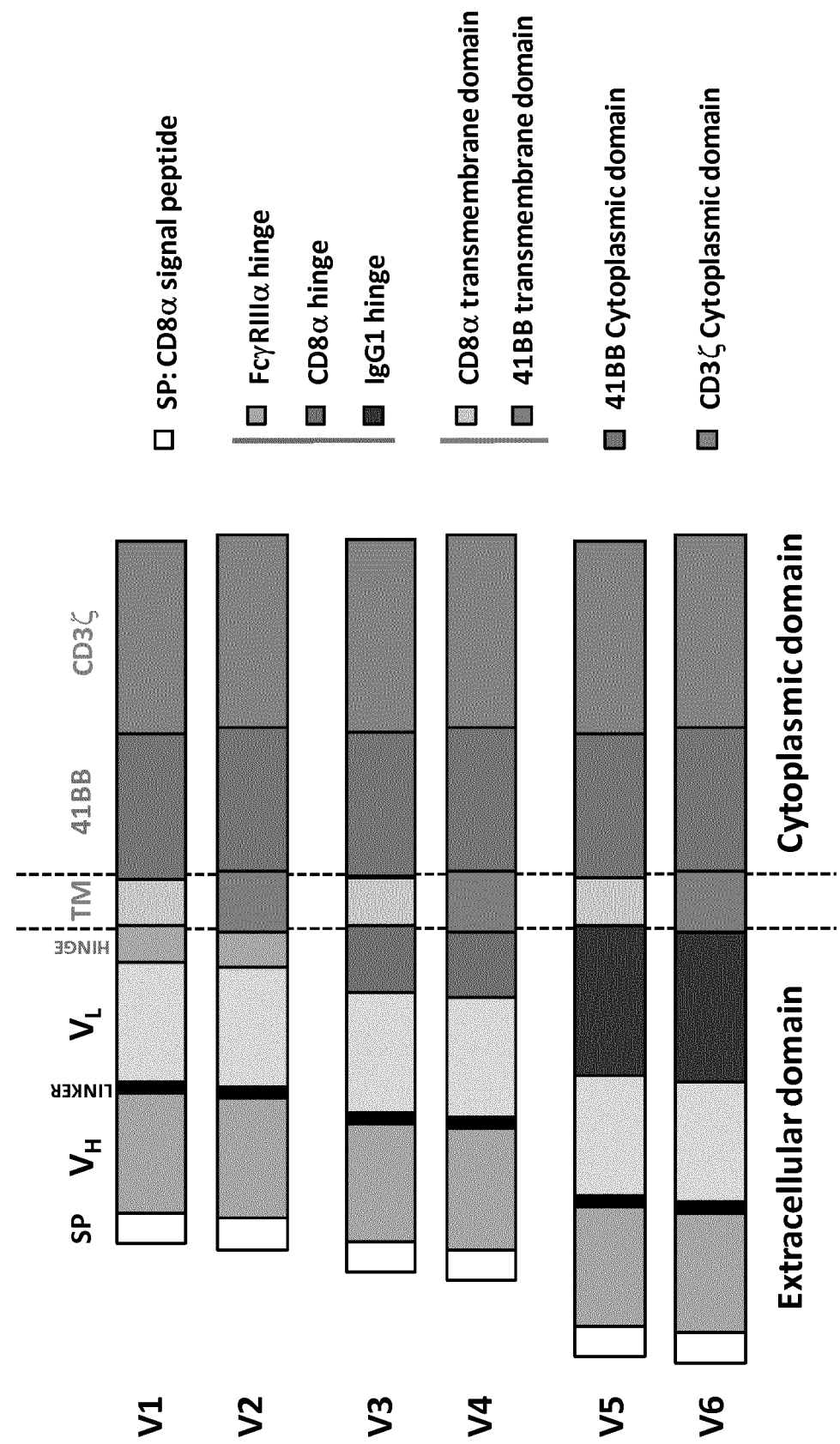

METHOD OF ENGINEERING DRUG-SPECIFIC HYPERSENSITIVE T-CELLS FOR IMMUNOTHERAPY BY GENE INACTIVATION

FIELD OF THE INVENTION

The present invention relates to the use of therapeutic cells for cell therapy or immunotherapy to treat patients in need, such as affected by cancer. In particular, the invention provides with a method of engineering immune cells (e.g. CAR T.-cells) by gene inactivation to render them sensitive to number of approved drugs. In case of adverse events or excessive immune response, these drugs can be administrated to the patient to deplete such engineered cells playing the role of "switch off" or "moderator". The invention opens the way to safer adoptive immunotherapy strategies for treating cancer.

BACKGROUND OF THE INVENTION

Adoptive immunotherapy, which involves the transfer of autologous or allogeneic antigen-specific immune cells generated ex vivo, is a promising strategy to treat cancer. The immune cells used for adoptive immunotherapy can be generated either by expansion of antigen-specific cells or redirection of such cells through genetic engineering (Park, Rosenberg et al. 2011). Transfer of viral antigen specific cells is a well-established procedure used for the treatment of transplant associated viral infections and rare viral-related malignancies. Similarly, isolation and transfer of tumor specific immune cells, in particular T-cells, has been shown to be successful in treating melanoma. Novel specificities in immune cells have been successfully generated through the genetic transfer of transgenic T cell receptors or chimeric antigen receptors (CARs). CARs are synthetic receptors consisting of a targeting moiety that is associated with one or more signaling domains in a single fusion molecule. CARs have successfully allowed T-cells and NK cells to be redirected against antigens expressed at the surface of tumor cells from various malignancies including lymphomas and solid tumors (Jena, Dotti et al. 2010).

T cell adoptive immunotherapy which involves the transfer of antigen-specific T-cells generated ex vivo, is a promising strategy to treat cancer. The T-cells used for adoptive immunotherapy can be generated through the genetic transfer of transgenic T cell receptors or chimeric antigen receptors (CARs). CARs are synthetic receptors consisting of a targeting moiety that is associated with one or more signaling domains. CARs have successfully allowed T-cells to be redirected against antigens expressed at the surface of tumor cells from various malignancies including lymphomas and solid tumors. However, despite their unprecedent efficacy for tumor eradication in vivo, CAR T cells can promote acute adverse events after being transferred into patients. On another hand, it would be desirable for doctors to have the possibility to reduce the engineered cells count in-vivo to modulate the immune response in accordance with the biological tests and monitoring performed on the patient during the course of the treatment. Among the potential adverse events are Graft versus host disease (GvHD), on-target off-tumor activity or aberrant lymphoproliferative capacity that may be due, among others, to vector derived insertional mutagenesis.

Thus, there is a need to develop cell specific depletion systems to prevent deleterious events to occur or to reduce the engineered cell count in vivo after engraftment of cells into a patient. Here, the inventors have thought about endowing engrafted cells with hypersensitivity properties toward a specific drug as an efficient solution to confer drug hypersensitivity to allogeneic cells.

The present invention relates on gene editing approaches, particularly adapted to immune primary cells, to create, or increase a pre-existing, sensitivity of the cells to approved drugs, to allow the depletion of said cells in response to said drugs during the course of a cell therapy.

SUMMARY OF THE INVENTION

In a general aspect, the present invention provides with methods of producing ex-vivo human cells, preferably immune cells, such as T cells, that can be depleted in-vivo as part of a cell therapy or immunotherapy treatment. Such treatment typically comprises a step of inducing a drug hypersensitivity into said human, preferably into immune cells, by selectively inactivating or inhibiting the expression of one gene involved in the metabolization, elimination or detoxification of said drug.

The inventors have sought for the inactivation of a selection of such gene, which actually conferred drug-specific hypersensitivity to engineered cells. In particular, inactivation of RhoA gene could be performed to genetically engineer human cells, preferably immune cells, in order to make them hypersensitive to doxorubicin. The inactivation of CDK5 gene conferred cell hypersensitivity to bortezomib. The inactivation of CXCR3, NR1H2, URG4, PARP14, AMPD3, CCDC38, NFU1 and/or CACNG gene conferred cell hypersensitivity to neratinib. The inactivation of GGH conferred hypersensitivity to 5-FU and resistance to methotrexate. The inactivation of SAMHD1 conferred hypersensitivity to deoxycytidine analogs, such as cytarabine (ara-C). These inactivations were effective in primary immune cells, in particular CAR T-cells used in immunotherapy.

The inhibition of expression of such gene(s) is preferably performed by gene editing, and in particular by introducing into said human cells at least one engineered rare-cutting endonucleases targeting said gene, such as TALE-nuclease, Zing Finger nuclease, RNA-guided endonucleases (e.g. Cas9 or Cpf1), Argonaute, or homing endonuclease.

The resulting drug-hypersensitive cells, especially the immune cells, can be further engineered to express a Chimeric Antigen Receptor (CAR) to direct their cytotoxicity towards unwanted cells (ie. tumoral cells) expressing particular surface antigen markers. Such engineered cells can be also modified to be less alloreactive by inactivating genes involved into the expression of T cell receptor (e.g. TCRalpha or TCRbeta) in view of their safer use in allogeneic treatment. Further genes may also be transiently or definitely inactivated such as those expressing immune-checkpoints (e.g. PD1)) to improve the tolerability of the engineered cells by the host organism.

The present invention relates also to an isolated human cell, preferably immune cell, made hypersensitive to a drug obtainable by the above method, a pharmaceutical composition containing same for its use in the treatment of cancer, infection or immune disease.

Furthermore, the present invention concerns the use of at least one isolated human cell, preferably immune cell that is hypersensitive to at least one drug in sequential combination with to at least one drug to which said immune cell has been made hypersensitive, for a safer cell therapy or immunotherapy treatment.

BRIEF DESCRIPTION OF THE FIGURE

FIG. 1: Schematic representation of the different single chain chimeric antigen receptor (scCAR) Architecture (V1 to V6), as preferred ones, which can arm the engineered immune cells according to the present invention. All these scCAR contain in their extracellular domain an antigen binding domain, typically a scFv of particular monoclonal antibodies, and a hinge, a transmembrane (TM) domain and an intracellular domain. They all contain in common the same scFv, TM domain (CD8alpha) and intracellular domain comprising typically the CD3 zeta transduction signaling domain and the 4-1 BB co-stimulatory domain. They differ by their hinge which can be of different length: CD8alpha, FcERIIIgamma or IgG1

DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Method of Engineering Drug-Specific Hypersensitive Cells for Depletion Purpose

To improve cell therapy and have the possibility of depleting engineered cells, —in particular T cells expressing a chimeric antigen receptor (CAR)—, the present invention provides as a solution to confer hypersensitivity of such cells to a specific drug, inactivating the expression of at least one or specific gene(s) involved in the metabolisation, excretion or detoxification of corresponding said drug(s).

In contrast to previous work done on the hypersensitivity reactions of immune cells (Pavlos R, Mallal S Ostrov D, Buus S, Metushi M, Peters B, and Phillips E, 2015, "T Cell-Mediated Hypersensitivity Reactions to Drugs", Annu Rev Med.; 66: 439-454), where hypersensitivity was regarded as an unwanted effect, the inventors have sought for conferring hypersensitivity to immune cells for their safer use in immunotherapy. In particular, the inactivation of specific genes directly or indirectly involved in some mechanisms of resistance to a number of approved drugs into said cells were successfully performed to obtain engineered cells hypersensitive to such drugs, suitable for engraftment therapy. Their approach is particularly relevant to allogeneic immune cells, but can be expanded to multiple situations where it is desirable to control the count of cells introduced into an organism as a therapeutic grade depletion system.

The present invention aims to improve security and control of cell therapy protocols. It can be practiced by proceedings with at least one of the following steps of:
  Selecting cells useful in a cell therapy program, which are found to be resistant to standard dose range of an approved drug;
  Proceeding to the specific Inactivation or repression of genes involved into the resistance mechanism of said cell to said approved drug, preferably by gene editing techniques;
  Assaying or screening the cells that have been engineered during the previous step with respect to said standard dose range of said approved drug;
  selecting the engineered cells that have become sensitive to said drug at a dose comprised into said standard dose range.

The resulting cells are deemed safer than the initial ones insofar as the cell therapy treatment can be controlled or interrupted in-vivo by using the approved drug.

According to one of its embodiments, the present invention relates to a method of producing a therapeutic reagent comprising human cells that may be depleted in-vivo as part of an cell therapy treatment, said method comprising:
  (a) Providing human cells;
  (b) Ex-vivo inducing specific drug hypersensitivity into said human cell by selectively inhibiting the expression of at least one gene, said gene being directly or indirectly involved in the metabolization, elimination or detoxification of said specific drug,
  (c) Optionally assaying the hypersensitivity to said drug of the cell engineered in step b);
  (d) culturing, and preferably expanding, the engineered human cells obtained in step b).

By "in vivo depletion of human cell", it is meant in the present invention that the depletion may be complete, almost complete or partial. The level of depletion depends of the therapeutic goal to achieve. By "complete in vivo depletion"—i.e 100% of the cells are depleted—applies particularly when engineered human cells—mainly immune cells—of the invention are found harmful against host cells (such as in a graft-versus-host event). A less stringent in vivo depletion of engineered cells may be performed to deplete more than 95% of engineered human cells of the present invention administrated to the patient. This almost complete depletion may be applied in case of an adverse event such a cytokine release storm (CRS) in which activated engineered immune cells administrated to the patient release cytokines, producing a type of systemic inflammatory response. Finally, a partial in depletion may be applied—at least of 50%—, when a modulation of the response of the engineered human cells, preferably immune cells, is sought. This modulation can be useful, for instance, to restrain the activity of CAR-T cells, when the latter have been found to be overaggressive (ie to limit "off targets").

According to a preferred embodiment, said in vivo depletion of human cells made drug-specific hypersensitive is performed to an extent that at least 50%, preferably 95% or more preferably 100% of the engineered cells are depleted.

Preferred human cells to be depleted according to the present invention are effector cells, in particular immune cells, preferably NK or T cells, and more preferably CD8+ T cells. The goal of the depletion can be to stop or mitigate adverse effects observed during the course of a treatment, or to adjust the number of cells (cell count) to modulate their overall activity as part of the treatment. The depletion of drug-specific hypersensitive immune cells may be monitored by analyzing biopsies or sampling at regular intervals by any suitable method known in the art.

The expression "specific-drug-specific hypersensitive human cell" corresponds to the human cell, preferably immune cell, which has been inactivated for at least one said drug-related gene.

By "inducing a drug hypersensitivity into a cell", it is meant that after being engineered by inactivation of at least one gene(s) involved in the metabolisation, excretion or detoxification of said drug (referred to herein as drug-related gene), the cell loses ability to metabolize, degrade or detoxify said drug or prodrug by lack or reduction of the expression of a suitable enzyme, in such a way that the drug accumulates or becomes toxic to the cell.

By "assaying the hypersensitivity of the human cell to said drug", it is meant that an in vitro test is performed by contacting said engineered human cells, preferably immune cells, with a series of different amounts of the drug and evaluating their survival rate i.e determination of IC50 or slope of the dose-response curve. Hypersensitivity to a specific drug is readily assessed by the decrease of the IC50 value. Such routine test can be performed according, i.e. to WO201575195.

To become hypersensitive to a given compound, the engineered cell must be more sensitive compared to the non-engineered one. Generally, the amount of drug used to kill on average 50% of the cells, referred to as the "IC50" dose, gets reduced by at least 20%, preferably by at least 30%, more preferably by at least 40%, even more preferably by at least 50%, 60%, 70%, 80% and even 90%, so that an actual effect of depletion can be obtained using this drug in-vivo.

Are contemplated within the present invention any type of human cell which may be used in cell therapy or cell immunotherapy, including stem cells which can be adult stem cells, induced pluripotent stem cells (iPS), embryonic stem cells, hematopoietic stem cell (HSCs), cord blood stem cells, progenitor cells, bone marrow stem cells, totipotent stem cells or hematopoietic stem cells. Also part of the present invention are different types of human cell which are transplanted for tissue repair—i.e heart, liver, kidney—for instance by using fetal precursor cell xenotransplants.

According to one embodiment, said human cells to be engineered to become specific drug-specific hypersensitive are human hematopoietic stem cells (HSCs). Human cell according to the present invention refers particularly to a cell of hematopoietic origin functionally involved in the initiation and/or execution of innate and/or adaptative immune response. This is advantageous because HSCs possess the ability to self-renew and differentiate into all types of blood cells, especially those involved in the human immune system. Thus, they can be used to treat blood and immune disorders.

According to a preferred embodiment, said human cells particularly suitable using the method of the invention, are human primary cells. By "primary cell" or "primary cells" are intended cells taken directly from living tissue (i.e. biopsy material) and established for growth in vitro for a limited amount of time, meaning that have undergone few population doublings and are therefore more representative of the main functional components and characteristics of tissues from which they are derived from. Primary cells can be opposed to continuous tumorigenic or artificially immortalized cell lines. Non-limiting examples of cell lines are CHO-K1 cells; HEK293 cells; Caco2 cells; U2-OS cells; NIH 3T3 cells; NSO cells; SP2 cells; CHO—S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells. Primary cells are generally preferred in therapy as they are more functional.

According to a more preferred embodiment, said human cells particularly suitable using the method of the invention, are human immune cells, such as T-cell obtained from a donor. Said T cell according to the present invention can be derived from a stem cell, such as adult stem cells, embryonic stem cells, induced pluripotent stem cells, cord blood stem cells, progenitor cells, bone marrow stem cells, totipotent stem cells or hematopoietic stem cells. Representative human stem cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes.

By "cell therapy" is meant in the following to include "cell immunotherapy".

The term "therapeutic reagent" refers particularly to a composition or formulation comprising engineered human cell, preferably immune cells, such as described in the present invention.

The terms "drug", "therapeutic agent" or "chemotherapeutic agent", or as used herein refers to a compound or a derivative thereof that can interact with a cancer cell, thereby reducing the proliferative status of the cell and/or killing the cell. Examples of chemotherapeutic agents include, but are not limited to, alkylating agents (e.g., cyclophosphamide, ifosamide), metabolic antagonists (e.g., methotrexate (MTX), 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, and the like. Such agents may further include, but are not limited to, the anti-cancer agents TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

By "inhibiting the expression of at least one gene", it is meant that the gene of interest is repressed or not expressed in a functional protein form. This inhibition can be obtained by gene silencing such as RNA interference, preferably shRNA, or by gene inactivation, e.g. by gene editing.

Therefore, in the following, the term "inhibition" is meant to include the aspect "inactivation".

According to one embodiment, shRNA can be used to inhibit gene expression to induce specific drug hypersensitivity in engineered human cells. As an alternative, siRNA may be used, although less appropriate due to its transient effect. Moreover, gene expression is dependent upon siRNA concentration. Thus, due to its ability to provide specific, long-lasting, gene silencing, it may be more appropriate to use shRNA. Expression of shRNA is typically accomplished by delivery of plasmids or through viral or bacterial vectors as described in the art (Paddison, P J et al, 2002, *Genes & Development* 16 (8): 948-58; Brummelkamp, T R et al, 2002, *Science* 296 (5567): 550-3).

According to one embodiment, wherein said gene inhibition in step (b) is a long term inhibition, preferably by shRNA interference, or permanent, preferably using a gene editing as detailed further on.

By "long term inhibition", it is meant that the level of expression of said gene is decreased by at least 25%, preferably 50%, and more preferably 75% compared to that of non-engineered human cell in the same conditions (ie. treatment, culture . . . ) over a period of time which is of several days, allowing the treatment to be effective, preferably over the life time of the human cell being administrated to the patient.

Inactivation of Gene Expression by Using Rare-Cutting Specific Endonuclease(s)

According to one preferred embodiment, the present invention relates to a method of producing a therapeutic reagent comprising human cells that may be depleted in-vivo as part of an cell therapy treatment, said method comprising:

(a) Providing human cells;

(b) Ex-vivo inducing specific drug hypersensitivity into said human cell by selectively inactivating the expression of at least one gene, said gene being directly or indirectly involved in the metabolization, elimination or detoxification of said specific drug, (c) Optionally assaying the hypersensitivity to said drug of the cell engineered in step b);

(d) Culturing, and preferably expanding, the engineered human cells obtained in step b).

By "inactivating a gene" it is intended that the gene of interest is not expressed in a functional protein form by disruption of at least one coding sequence of said gene, for instance by using gene editing techniques.

According to a preferred embodiment, gene editing is used to inhibit gene expression to induce specific drug hypersensitivity in engineered human cells.

In more specific embodiments, the method for engineering cells according to the present invention relies on the expression, in the provided cells to engineer, of one rare-cutting endonuclease, such that said rare-cutting endonuclease specifically catalyzes cleavage in one targeted gene, thereby inactivating by mutagenesis the expression of said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts (KO). Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art.

In one embodiment, the step of inactivation of at least a gene to confer specific drug-hypersensitivity into the human cells of each individual sample comprises introducing into the cell a rare-cutting endonuclease able to specifically disrupt at least one gene encoding a polypeptide (ie enzyme) which is implicated in the metabolization, elimination or detoxification of said drug.

In another embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene implicated as a drug specific metabolization-related gene.

In a more particular embodiment, said human cells are transformed with nucleic acid encoding a rare-cutting endonuclease capable of specifically disrupting a drug related gene(s), so that said rare-cutting endonuclease is expressed into said cells and introduces mutations into said gene(s). Said rare-cutting endonuclease can be a meganuclease, a Zinc finger nuclease, a MBBBD-nuclease, a TALE-nuclease or a RNA guided endonuclease, such as Cas9 or Cfp1 (Cong L., et al., (2013) Multiplex genome engineering using CRISPR/Cas systems. Science 339:819-823; Zetsche, B. et al. (2015) Cpf1 is a single RNA-guided endonuclease of a class2 CRISPR-Cas system. *Cell* 163:759-771). In a preferred embodiment, said rare-cutting endonuclease is a TALE-nuclease. In some instances, mutagenesis can be performed by using a targeted nickase or a pair of such targeted nickase to obtain gene deletions.

In a preferred embodiment, said a rare-cutting endonuclease comprises a TALE-binding domain such as the reagents referred to MegaTAL (Boissel et al., (2014) Mega-TALs: a rare-cleaving nuclease architecture for therapeutic genome engineering. *Nucl. Acids Res.* 42 (4): 2591-2601.), Cas9 or Cpf1, and more preferably to TALE-nucleases (WO2011072246).

By TALE-nuclease is intended a fusion protein consisting of a DNA-binding domain derived from a Transcription Activator Like Effector (TALE) and one nuclease catalytic domain to cleave a nucleic acid target sequence (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012). In the present invention new TALE-nucleases have been designed for precisely targeting relevant genes for adoptive immunotherapy strategies.

Additional catalytic domain can be further introduced into the cell with said rare-cutting endonuclease to increase mutagenesis in order to enhance their capacity to inactivate targeted genes. In particular, said additional catalytic domain is a DNA end processing enzyme. Non limiting examples of DNA end-processing enzymes include 5-3' exonucleases, 3-5' exonucleases, 5-3' alkaline exonucleases, 5' flap endonucleases, helicases, phosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast Exol (EXO1_YEAST), *E. coli* Exol, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain is TREX, more preferably TREX2 catalytic domain (WO2012/058458). In another preferred embodiment, said catalytic domain is encoded by a single chain TREX2 polypeptide. Said additional catalytic domain may be fused to a nuclease fusion protein or chimeric protein according to the invention optionally by a peptide linker.

Endonucleolytic breaks are known to stimulate the rate of homologous recombination. Thus, in another embodiment, the genetic modification step of the method further comprises a step of introduction into cells of an exogenous nucleic acid comprising at least a sequence homologous to a portion of the target nucleic acid sequence, such that homologous recombination occurs between the target nucleic acid sequence and the exogenous nucleic acid.

The invention provides with a selection of genes, which expression can be inactivated in immune cells without adverse consequences, conferring human cells with hypersensitivity to drugs, said selection comprising the genes encoding: RhoA, CDK5, CXCR3, NR1H2, URG4, PARP14, AMPD3, CCDC38, NFU1 and/or CACNG, GGH and SAMHD1.

Preferred TALE-nucleases according to the invention are those recognizing and cleaving at least one target sequence having identity with one selected from the group consisting of: SEQ ID NO: 14 or 15 (GGH), SEQ ID NO: 1 or 2 (RhoA), SEQ ID NO: 3, 4 or 5 (CDK5), SEQ ID NO:6 or 7 (CXCR3), SEQ ID NO: 20 (NR1H2), SEQ ID NO: 18 or 19 (URG4), SEQ ID NO:16 or 17 (PARP14), SEQ ID NO: 21, 22 or 23 (AMPD3), SEQ ID NO: 8 or 9 (CCDC38), SEQ ID NO: 10 or 11 (NFU1), and SEQ ID NO: 12 or 13 (CACNG5).

According to a further embodiment of the invention, the engineered cells of the invention combine several inactivations in distinct genes, preferably induced by specific rare-cutting endonucleases into at least a first gene, said first gene inactivation conferring hypersensitivity to a first specific corresponding drug, and said at least additional gene inactivation conferring resistance to another specific corresponding drug. Preferably such second drug, to which engineered cells of the invention are resistant, is used in a combination therapy with said cells. Said second drug may be used prior to, during, or after the administration of the engineered cells of the invention, for instance, as part a lymphodepletion and/or chemotherapy treatment.

The following paragraphs detail the preferred inhibition according to the invention of a selection of genes, particularly applicable to immune cells.

Inhibition of GGH Expression to Confer Hypersensitivity to 5-FU and/or Resistance to Methotrexate (MTX)

According to a preferred embodiment, the present invention provides a method of producing human cells that may be depleted in-vivo as part of a cell therapy treatment, said method comprising
(a) Providing human cells;
(b) Ex-vivo inducing 5-FU specific hypersensitivity and/or methotrexate specific resistance into said human cell by selectively inhibiting or inactivating the expression of the gene encoding GGH, (c) Optionally assaying said hypersensitivity of said human cell engineered in step b) to said corresponding drugs i.e. 5-FU an methotrexate;
(d) Culturing, and preferably expanding, the engineered immune cells obtained in step b).

Said method can be used to produce engineered cells for treating cancer, infection or immune disease in a patient by unique or sequential administration thereof to a patient.

According to a preferred embodiment, the immune cells according to the present invention, which expression of GGH is inhibited, are administered to the patient prior to their elimination by the drug 5-FU.

Human GGH (gamma-glutamyl hydrolase, with UniProtKB reference: Q92820 and RefSeq reference locus: NM_003878) is known to catalyze the cleavage of a gamma-linked glutamate bond. The gene may play an important role in the bioavailability of dietary pteroylpolyglutamates and in the metabolism of pteroylpolyglutamates and antifolates (Galivan J et al, *Semin. Oncol.* 26 (2 Suppl 6): 33-7). Inhibition or inactivation of GGH has been found by the inventors to confer sensitivity of cells derived from lymphoid progenitor cells, such as NK cells and T cells, to 5-fluorouracil (5-FU).

According to a more preferred embodiment, said human GGH enzyme inhibition is performed by a least one rare-cutting endonuclease targeting a sequence comprised into a sequence having at least 80%, preferably 90%, more preferably 95% and mostly preferably 99% identity with SEQ ID NO. 14 or NO. 15.

And, to modulate or terminate the treatment, further administration of 5-FU to which said cells have been made hypersensitive in order to deplete in vivo said cells. 5-FU is a drug that is a pyrimidine analog part of family of antimetabolites drugs acting through irreversible inhibition of thymidylate synthase as described by Longley D. B., et al. (2003). "*5-fluorouracil: mechanisms of action and clinical strategies*". Nat. Rev. Cancer 3 (5): 330-8).

A dose ranging between 185 and 555 mg/m2, advantageously between 370 and 444 mg/m2 of 5-FU may be administered to the patient per injection. The administration is usually per intravenous injection, but can be performed by intra-arterial infusion and may be redone after an interval of 4 to 6 weeks from the last dose if necessary.

According to another preferred embodiment, said expression of GGH is inhibited conferring hypersensitivity to 5-FU and resistance to methotrexate. Inhibition or inactivation of GGH was found by the inventors to confer sensitivity of cells derived from lymphoid progenitor cells, such as NK cells and T cells, to methotrexate. This drug is an antimetabolite and antifolate drug acting by inhibiting the metabolism of folic acid via dihydrofolate reductase (Takimoto C H eta, 1996 *Oncologist* 1 (1 & 2): 68-81). This drug is currently used in treatment of cancer or autoimmune diseases. (reviewed in *Joint Formulary Committee* (2013). British National Formulary (BNF) (65 ed.). London, UK: Pharmaceutical Press. ISBN 978-0-85711-084-8).

A dose ranging between 10 and 12.000 mg/m2 of methotrexate, the higher dosages with leucovorin rescue, advantageously between 30 and 40 mg/m2 of methotrexate may be administered to the patient per os (PO) or per IM injection. The administration is usually performed for a period of 5 days, and may be repeated.

As a preferred embodiment, the invention provides the administration of an immune cell made hypersensitive to 5-FU drug by inactivating of the gene encoding GGH, said cell being further engineered to endow a chimeric antigen receptor (CAR) against a cancerous cell, an infectious agent or a dysfunctioning host immune cell.

The terms "dysfunctioning host immune cell" focuses particularly to host immune cells which engender autoimmune diseases such as for instance self-reactive T-cells.

In particular, said further genetic engineered of cells according to the present invention, in addition to the GGH inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

The engineered cells according to the present invention can advantageously combine a first gene inactivation into a gene encoding GGH to confer hypersensitivity to 5-FU and/or resistance to methotrexate, and a further genetic engineering to confer specific resistance to another drug, such additional modification may be performed by a gene inactivation or by gene overexpression for instance of a mutant form of a gene, said gene being involved in the metabolization of said drug.

In a more particular embodiment, said engineered cells of the present invention can advantageously combine a first gene inactivation into a gene encoding GGH to confer hypersensitivity to 5-FU and/or resistance to methotrexate and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)— such as clofarabine or fludarabine—, corticosteroids, alemtuzumab respectively.

In another particular embodiment, said engineered cells of the present invention can advantageously combine a first gene inactivation into a gene encoding GGH to confer hypersensitivity to 5-FU and/or resistance to methotrexate, and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding GGH to confer hypersensitivity to 5-FU and/or resistance to methotrexate, and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195), As exemplary embodiments, said engineered cells of the present invention can combine a first gene inactivation into a gene encoding GGH to confer hypersensitivity to 5-FU and/or resistance to methotrexate, and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of RhoA Expression to Confer Hypersensitivity to Doxorubicin

According to a preferred embodiment, the present invention provides a method of producing human cells that may be depleted in-vivo as part of a cell therapy treatment, said method comprising:

(a) Providing human cells;

(b) Ex-vivo inducing doxorubicin specific hypersensitivity into said human cell by selectively inhibiting or inactivating the expression of RhoA gene;

(c) Optionally assaying the hypersensitivity of said human cell engineered in step b) to said drug;

(d) Culturing, and preferably expanding, the engineered immune cells obtained in step b).

Said method can be used to produce engineered cells for treating cancer, infection or immune disease in a patient by unique or sequential administration thereof to a patient. Human RhoA encodes a small GTPases (Uniprot ref: P61586) which cycles between inactive GDP-bound and active GTP-bound states and function as molecular switches in signal transduction cascades. Rho proteins promote reorganization of the actin cytoskeleton and regulate cell shape, attachment, and motility. Knockdown of RhoA was shown to increase the activation of the nuclear factor-KB pathway, as well as the activity of nitric oxide synthase in colorectal cancer cell lines. Such alterations was found to favor the tyrosine nitration of the multidrug resistance protein 3 transporter (MRP3) and contributed to a reduced doxorubicin efflux. In addition, RhoA expressions in T cells and in colorectal cancer are similar (Doublier, Riganti et al. 2008).

Inhibition or inactivation of RhoA has been found by the inventors to confer sensitivity of cells derived from lymphoid progenitor cells, such as NK cells and T cells, to doxorubicin.

According to a preferred embodiment, the immune cells according to the present invention, which expression of RhoA is inhibited or inactivated, are administered to the patient prior to their elimination by the drug doxorubicin.

According to a preferred embodiment, said human RhoA inhibition is performed by a least one rare-cutting endonuclease directed against a target sequence comprised into the NCBI Reference Sequence NM_001664.

According to a more preferred embodiment, said human RhoA inhibition is performed by a least one rare-cutting endonuclease targeting a sequence comprised into a sequence having at least 80%, preferably 90%, more preferably 95% and mostly preferably 99% identity with SEQ ID NO. 1 or 2.

And, to modulate or terminate the treatment, a further administration of doxorubicin to which said cells have been made sensitive to may be performed in order to deplete in vivo said cells.

According to a preferred embodiment, said immune cell being administered to the patient beforehand, which comprises administering to a patient the drug doxorubicin in case of occurrence of an adverse event. Doxorubicin is an anthracycline antitumor antibiotic functioning by intercalating DNA (reviewed in *Martindale: The Complete Drug Reference. Pharmaceutical Press*). This drugs is commonly used in the treatment of a wide range of cancers, including hematological malignancies (blood cancers, like leukemia and lymphoma), many types of carcinoma (solid tumors) and soft tissue sarcomas. This drug is also often used in combination chemotherapy as a component of various chemotherapy regimens (reviewed in Medscape Reference, WebMD).

A dose ranging between 30 and 75 mg/m² of doxorubicin advantageously between 40 and 60 of doxorubicin may be administrated to the patient per injection. The administration is usually per intravenous injection, but can be performed by intra-arterial infusion and may be redone after an interval of 4 to 6 weeks from the last dose if necessary.

As a preferred embodiment, the invention provides the administration of an immune cell made hypersensitive to doxorubicin drug by inactivating of the gene encoding RhoA, said cell being further engineered to endow a chimeric antigen receptor (CAR) against a cancerous cell, an infectious agent or a dysfunctioning host immune cell.

In particular, said further genetic engineered of cells according to the present invention, in addition to the RhoA inhibition or inactivation, confers resistance to a drug selected in the group consisting of alkylating agents (e.g., cyclophosphamide, isophosphamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

The engineered cells according to the present invention can advantageously combine a first gene inactivation into a gene encoding RhoA to confer hypersensitivity to doxorubicin and a further genetic engineering to confer specific resistance to another drug, such additional modification may be performed by a gene inactivation or by gene overexpression for instance of a mutant form of a gene, said gene being involved in the metabolization of said drug.

In a more particular embodiment, said engineered cells of the present invention can advantageously combine a first gene inactivation into a gene encoding RhoA to confer hypersensitivity to doxorubicin, and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding RhoA to confer hypersensitivity to doxorubicin and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding RhoA to confer hypersensitivity to doxorubicin and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195), As exemplary embodiments, said engineered cells of the present invention can combine a first gene inactivation into a gene encoding RhoA to confer hypersensitivity to doxorubicin and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of CDK5 Expression to Confer Hypersensitivity to Bortezomib

According to a preferred embodiment, the present invention provides a method of producing human cells that may be depleted in-vivo as part of a cell therapy treatment, said method comprising:

(a) Providing human cells;
(b) Ex-vivo inducing bortezomib specific hypersensitivity into said human cell by selectively inhibiting the expression of CDK5 gene, and
(c) Optionally assaying the hypersensitivity of said human cell engineered in step b) to said drug;
(d) Culturing, and preferably expanding, the engineered immune cells obtained in step b).

Said method can be used to produce engineered cells for treating cancer, infection or immune disease in a patient by unique or sequential administration thereof to a patient.

Human CDK5 (NP_001157882) encodes a proline-directed serine/threonine kinase (UniProt: Q00535) that is a member of the cyclin-dependent kinase family of proteins. Unlike other members of the family, the protein encoded by this gene does not directly control cell cycle regulation. Instead, the protein, which is predominantly expressed at high levels in mammalian post mitotic central nervous system neurons, functions in diverse processes such as synaptic plasticity and neuronal migration through phosphorylation of proteins required for cytoskeletal organization, endocytosis and exocytosis, and apoptosis.

Inhibition or inactivation of CDK5 has been found by the inventors to confer sensitivity of cells derived from lymphoid progenitor cells, such as NK cells and T cells, to bortezomib. Bortezomib is a modified dipeptidyl boronic acid corresponding to a therapeutic proteasome inhibitor, therefore interrupting this process and letting those proteins kill the cancer cells (Bonvini P, et al, 2007, *Leukemia* 21 (4):

838-42). It is approved in the U.S. for treating relapsed multiple myeloma and mantle cell lymphoma (Takimoto C H et al, 2008, Cancer Management: A Multidisciplinary Approach. 11 ed).

According to a preferred embodiment, said human CDK5 inhibition is performed by a least one rare-cutting endonuclease directed against a target sequence comprised into the NCBI Reference Sequence RefSeq NP_001157882.

According to a more preferred embodiment, said human CDK5 inhibition is performed by a least one rare-cutting endonuclease targeting a polynucleotide sequence comprised into a sequence having at least 80%, preferably 90%, more preferably 95% and mostly preferably 99% identity with SEQ ID NO. 3, NO. 4, NO. 5 or NO. 6.

According to a preferred embodiment, the immune cells according to the present invention, which expression of CDK5 is inhibited or inactivated, are administered to the patient prior to their elimination by the drug bortezomib.

And, to modulate or terminate the treatment, further administration of bortezomib to which said cells have been made sensitive may be performed in order to deplete in vivo said cells.

A dose ranging between 0.5 and 2.0 mg/m2 of bortezomib, advantageously between 1.3 mg/m2 of doxorubicin may be administrated to the patient per injection. The administration is usually per intravenous injection, and may be redone twice weekly after an interval of 2-3 weeks from the last dose if necessary.

As a preferred embodiment, the invention provides the administration of an immune cell made hypersensitive to bortezomib drug by inactivating of the gene encoding CDK5, said cell being further engineered to endow a chimeric antigen receptor (CAR) against a cancerous cell, an infectious agent or a dysfunctioning host immune cell.

The engineered cells according to the present invention can advantageously combine a first gene inactivation into a gene encoding CDK5 to confer hypersensitivity to bortezomib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the CDK5 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding CDK5 to confer hypersensitivity to bortezomib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding CDK5 to confer hypersensitivity to bortezomib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding CDK5 to confer hypersensitivity to bortezomib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195), As exemplary embodiments, said engineered cells of the present invention can combine a first gene inactivation into a gene encoding CDK5 to confer hypersensitivity to bortezomib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of CXCR3 Expression to Confer Hypersensitivity to Neratinib

According to a preferred embodiment, the present invention provides a method of producing human cells that may be depleted in-vivo as part of a cell therapy treatment, said method comprising:

(a) Providing human cells;

(b) Ex-vivo inducing neratinib specific hypersensitivity into said human cell by selectively inhibiting or inactivating the expression of CXCR3 gene, and (c) Optionally assaying the hypersensitivity of said human cell engineered in step b) to said drug;

(d) Expanding the engineered immune cells obtained in step b).

Human CXCR3 (Refseq mRNA: NM_001142797) encodes for protein-coupled receptor in the CXC chemokine receptor family. CXCR3 is expressed primarily on activated T lymphocytes and NK cells and some epithelial cells (Qin S, et al, 1998. J. Clin. Invest. 101 (4): 746-5). CXCR3 is able to regulate leukocyte trafficking. Inhibition or inactivation of CXCR3 has been found by the inventors to confer sensitivity of cells derived from lymphoid progenitor cells, such as NK cells and T cells, to neratinib.

According to a preferred embodiment, said human CXCR3 inactivation is performed by a least one rare-cutting endonuclease directed against a target sequence comprised into the NCBI Reference Sequence RefSeq NM_001142797.

According to a more preferred embodiment, said human CXCR3 inactivation is performed by a least one rare-cutting endonuclease targeting a polynucleotide sequence comprised into a sequence having at least 80%, preferably 90%, more preferably 95% and mostly preferably 99% identity with SEQ ID NO. 6, or NO. 7.

According to a preferred embodiment, the immune cells according to the present invention, which expression of CXCR3 is inhibited or inactivated, are administered to the patient prior to their elimination by the drug neratinib. Therefore, to modulate or terminate the treatment, further administration of neratinib to which said cells have been made sensitive may be performed in order to deplete in vivo said cells.

Neratinib (HKI-272) is a tyrosine kinase inhibitor under investigation for the treatment of breast cancer and other solid tumors. It is a dual inhibitor of the human epidermal growth factor receptor 2 (Her2) and epidermal growth factor receptor (EGFR) kinases (Rabindran S K, et al., 2004, Cancer Res. 64 (11): 3958-65.). This drug is currently assayed in clinical trial to treat patients with early-stage HER2-positive breast cancer (Breast cancer study aims to speed drugs, cooperation, Reuters, March 2010).

Said method can be used to produce engineered cells for treating cancer, infection or immune disease in a patient by unique or sequential administration thereof to a patient.

As a preferred embodiment, the invention provides the administration of an immune cell made hypersensitive to neratinib drug by inactivating or inhibiting the gene encoding for CXCR3, said cell being further engineered to endow a chimeric antigen receptor (CAR) against said cancerous cell, infectious agent or dysfunctioning host immune cell;

The engineered cells according to the present invention can advantageously combine a first gene inactivation into a gene encoding CXCR3 to confer hypersensitivity to neratinib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the CXCR3 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding CXCR3 to confer hypersensitivity to neratinib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding CXCR3 to confer hypersensitivity to neratinib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding CXCR3 to confer hypersensitivity to neratinib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding CXCR3 to confer hypersensitivity to neratinib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of CCDC38 Expression to Confer Hypersensitivity to Neratinib

According to a preferred embodiment, the present invention provides a method of producing human cells that may be depleted in-vivo as part of a cell therapy treatment, said method comprising:
   (a) Providing human cells;
   (b) Ex-vivo inducing neratinib specific hypersensitivity into said human cell by selectively inhibiting the expression of a gene encoding CCDC38, and
   (c) Optionally assaying the hypersensitivity of said human cell engineered in step b) to said drug;
   (d) Culturing, and preferably expanding, the engineered immune cells obtained in step b).

Human CCDC38 protein with UniProt reference Q502W7 is encoded by the gene under RefSeq NM_182496. Although the function of CCDC38 is not yet well understood, members of the coiled-coil domain protein family are known to have a role in cell motor activity (e.g. myosin) (Burkhard P et al, 2001, Trends Cell Biol 11: 82-88).

According to a preferred embodiment, said human CCDC38 inhibition is performed by a least one rare-cutting endonuclease directed against a target sequence comprised into the NCBI Reference Sequence RefSeq NM_182496.

According to a more preferred embodiment, said human CCDC38 inhibition is performed by a least one rare-cutting endonuclease targeting a polynucleotide sequence comprised into a sequence having at least 80%, preferably 90%, more preferably 95% and mostly preferably 99% identity with SEQ ID NO. 8 or SEQ ID NO. 9.

According to a preferred embodiment, the immune cells according to the present invention, which expression of CCDC38 is inhibited, are administered to the patient prior to their elimination by the drug neratinib. Inhibition or inactivation of CCDC38 has been found by the inventors to confer sensitivity of cells derived from lymphoid progenitor cells, such as NK cells and T cells, to neratinib.

And, to modulate or terminate the treatment, further administration of neratinib to which said cells have been made sensitive may be performed in order to deplete in vivo said cells.

Said method can be used to produce engineered cells for treating cancer, infection or immune disease in a patient by unique or sequential administration thereof to a patient.

As a preferred embodiment, the invention provides the administration of an immune cell made hypersensitive to neratinib drug by inactivating of the gene encoding CCDC38, said cell being further engineered to endow a chimeric antigen receptor (CAR) against said cancerous cell, infectious agent or dysfunctioning host immune cell.

The engineered cells according to the present invention can advantageously combine a first gene inactivation into a gene encoding CCDC38 to confer hypersensitivity to neratinib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the CCDC38 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding CCDC38 to confer hypersensitivity to neratinib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding CCDC38 to confer hypersensitivity to neratinib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding CCDC38 to confer hypersensitivity to neratinib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding CCDC38 to confer hypersensitivity to neratinib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of NFU-1 Expression to Confer Hypersensitivity to Neratinib

According to a preferred embodiment, the present invention provides a method of producing human cells that may be depleted in-vivo as part of a cell therapy treatment, said method comprising:
 (a) Providing human cells;
 (b) Ex-vivo inducing specific drug hypersensitivity into said human cell by selectively inhibiting the expression of a gene encoding NFU-1, and
 (c) Optionally assaying the hypersensitivity of said human cell engineered in step b) to said drug;
 (d) Culturing, and preferably expanding, the engineered immune cells obtained in step b).

Human NFU-1 with UniProt reference Q9UMS0 is encoded by the gene with reference NM_015700. This gene encodes a protein that is localized to mitochondria and plays a critical role in iron-sulfur cluster biogenesis diseases associated with NFU-1 include multiple mitochondrial dysfunctions syndrome 1 and fatal multiple mitochondrial dysfunction syndrome type 1 (Navarro-Sastre A et al; 2011, Am J Hum Genet. 89(5):656-67).

According to a preferred embodiment, said human NFU-1 inhibition is performed by a least one rare-cutting endonuclease directed against a target sequence comprised into the NCBI Reference Sequence RefSeq NM_015700.

According to a more preferred embodiment, said human NFU-1 inhibition is performed by a least one rare-cutting endonuclease targeting a polynucleotide sequence comprised into a sequence having at least 80%, preferably 90%, more preferably 95% and mostly preferably 99% identity with SEQ ID NO. 10, or NO. 11.

According to a preferred embodiment, the immune cells according to the present invention, which expression of NFU-1 is inhibited, are administered to the patient prior to their elimination by the drug neratinib. Inhibition or inactivation of NFU-1 has been found by the inventors to confer sensitivity of cells derived from lymphoid progenitor cells, such as NK cells and T cells, to neratinib. Thus, to modulate or terminate the treatment, further administration of neratinib to which said cells have been made sensitive may be performed in order to deplete in vivo said cells.

Said method can be used to produce engineered cells for treating cancer, infection or immune disease in a patient by unique or sequential administration thereof to a patient.

As a preferred embodiment, the invention provides the administration of an immune cell made hypersensitive to neratinib drug by inactivating of the gene encoding NFU-1, said cell being further engineered to endow a chimeric antigen receptor (CAR) against said cancerous cell, infectious agent or dysfunctioning host immune cell;

The engineered cells according to the present invention can advantageously combine a first gene inactivation into a gene encoding NFU-1 to confer hypersensitivity to neratinib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the NFU-1 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding NFU-1 to confer hypersensitivity to neratinib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding NFU-1 to confer hypersensitivity to neratinib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding NFU-1 to confer hypersensitivity to neratinib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding NFU-1 to confer hypersensitivity to neratinib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of URG4 Expression to Confer Hypersensitivity to Neratinib

According to a preferred embodiment, the present invention provides a method of producing human cells that may be depleted in-vivo as part of a cell therapy treatment, said method comprising:

(a) Providing human cells;

(b) Ex-vivo inducing neratinib specific hypersensitivity into said human cell by selectively inhibiting the expression of a gene encoding URG4, and (c) Optionally assaying the hypersensitivity of said human cell engineered in step b) to said drug;

(d) Culturing, and preferably expanding, the engineered immune cells obtained in step b).

Human URG4 with UniProt reference Q8TCY9 is encoded by gene with RefSeq reference NM_001077663. Overexpression of URG4/URGCP in the presence of HBV X protein may function as a putative oncogene that significantly contributes to multi-step hepatocarcinogenesis (Tufan N L et al, 2002, Neoplasia. 4(4):355-68).

According to a preferred embodiment, said human URG4 inhibition is performed by a least one rare-cutting endonuclease directed against a target sequence comprised into the NCBI Reference Sequence RefSeq M_001077663.

According to a more preferred embodiment, said human URG4 inhibition is performed by a least one rare-cutting endonuclease targeting a polynucleotide sequence comprised into a sequence having at least 80%, preferably 90%, more preferably 95% and mostly preferably 99% identity with SEQ ID NO. 18, or NO. 19.

According to a preferred embodiment, the immune cells according to the present invention, which expression of URG4 is inhibited, are administered to the patient prior to their elimination by the drug neratinib. Inhibition or inactivation of URG4 has been found by the inventors to confer sensitivity of cells derived from lymphoid progenitor cells, such as NK cells and T cells, to neratinib. Thus, to modulate or terminate the treatment, further administration of neratinib to which said cells have been made sensitive may be performed in order to deplete in vivo said cells.

Said method can be used to produce engineered cells for treating cancer, infection or immune disease in a patient by unique or sequential administration thereof to a patient.

As a preferred embodiment, the invention provides the administration of an immune cell made hypersensitive to neratinib drug by inactivating of the gene encoding URG4, said cell being further engineered to endow a chimeric antigen receptor (CAR) against said cancerous cell, infectious agent or dysfunctioning host immune cell;

The engineered cells according to the present invention can advantageously combine a first gene inactivation into a gene encoding URG4 to confer hypersensitivity to neratinib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the URG4 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding URG4 to confer hypersensitivity to neratinib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine, corticosteroids, alemtuzumab respectively.

In another particular embodiment, said engineered cells of the present invention can advantageously combine a first gene inactivation into a gene encoding URG4 to confer hypersensitivity to neratinib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding URG4 to confer hypersensitivity to neratinib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding URG4 to confer hypersensitivity to neratinib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of PARP14 Expression to Confer Hypersensitivity to Neratinib

According to a preferred embodiment, the present invention provides a method of producing human cells that may be depleted in-vivo as part of a cell therapy treatment, said method comprising:

(a) Providing human cells;

(b) Ex-vivo inducing neratinib specific hypersensitivity into said human cell by selectively inhibiting the expression of a gene encoding PARP14, and (c) Optionally assaying the hypersensitivity of said human cell engineered in step b) to said drug;

(d) Culturing, and preferably expanding, the engineered immune cells obtained in step b).

Human PARP14 with UniProtKB reference Q460N5 is encoded by gene having RefSeq DNA sequence NM_017554. Poly (ADP-ribose) polymerase (PARP) catalyzes the post-translational modification of proteins by the addition of multiple ADP-ribose moieties. In Hoon Cho S et al, 2013, J Immunol.; 191(6): 3169-3178, by inactivating PARP14, it is reported that this gene is implicated in B cell intrinsic and extrinsic regulation of antibody responses, influencing the class distribution, affinity repertoire, and recall capacity of antibody responses in mice PARP inhibitors are being developed for use in a number of pathologies including cancer, diabetes, stroke and cardiovascular disease.

According to a preferred embodiment, said human PARP14 inhibition is performed by a least one rare-cutting endonuclease directed against a target sequence comprised into the NCBI Reference Sequence RefSeq NM_017554.

According to a more preferred embodiment, said human PARP14 inhibition is performed by a least one rare-cutting endonuclease targeting a polynucleotide sequence comprised into a sequence having at least 80%, preferably 90%, more preferably 95% and mostly preferably 99% identity with SEQ ID NO. 16, or NO. 17.

According to a preferred embodiment, the immune cells according to the present invention, which expression of PARP14 is inhibited, are administered to the patient prior to their elimination by the drug neratinib. Inhibition or inactivation of PARP14 has been found by the inventors to confer hypersensitivity of cells derived from lymphoid progenitor cells, such as NK cells and T cells, to neratinib. Thus, to modulate or terminate the treatment, further administration of neratinib to which said cells have been made sensitive may be performed in order to deplete in vivo said cells.

Said method can be used to produce engineered cells for treating cancer, infection or immune disease in a patient by unique or sequential administration thereof to a patient.

As a preferred embodiment, the invention provides the administration of an immune cell made hypersensitive to neratinib drug by inactivating of the gene encoding PARP14, said cell being further engineered to endow a chimeric antigen receptor (CAR) against said cancerous cell, infectious agent or dysfunctioning host immune cell.

The engineered cells according to the present invention can advantageously combine a first gene inactivation into a gene encoding PARP14 to confer hypersensitivity to neratinib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the PARP14 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding PARP14 to confer hypersensitivity to neratinib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding PARP14 to confer hypersensitivity to neratinib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding PARP14 to confer hypersensitivity to neratinib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding PARP14 to confer hypersensitivity to neratinib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of AMPD3 to Confer Hypersensitivity to Neratinib

According to a preferred embodiment, the present invention provides a method of producing human cells that may be depleted in-vivo as part of a cell therapy treatment, said method comprising:

(a) Providing human cells;

(b) Ex-vivo inducing neratinib specific hypersensitivity into said human cell by selectively inhibiting the expression of a gene encoding AMPD3, and (c) Optionally assaying the hypersensitivity of said human cell engineered in step b) to said drug;

(d) Culturing, and preferably expanding, the engineered immune cells obtained in step b).

According to an embodiment, said gene which expression is inhibited is AMPD3. Human AMPD3 having UniProt reference Q01432 is a member of the AMP deaminase gene family. The encoded protein is a highly regulated enzyme that catalyzes the hydrolytic deamination of adenosine monophosphate to inosine monophosphate, a branch point in the adenylate catabolic pathway (Yamada, Y et al, 1992, Biochim. Biophys. Acta 1171: 125-128).

According to a preferred embodiment, said human AMPD3 inhibition is performed by a least one rare-cutting endonuclease directed against a target sequence comprised into the NCBI Reference Sequence RefSeq NM_000480.

According to a more preferred embodiment, said human AMPD3 inhibition is performed by a least one rare-cutting endonuclease targeting a polynucleotide sequence comprised into a sequence having at least 80%, preferably 90%, more preferably 95% and mostly preferably 99% identity with SEQ ID NO. 21, NO. 22 or SEQ ID NO. 23.

According to a preferred embodiment, the immune cells according to the present invention, which expression of AMPD3 is inhibited, are administered to the patient prior to their elimination by the drug neratinib. Inhibition or inactivation of AMPD3 has been found by the inventors to confer sensitivity of cells derived from lymphoid progenitor cells, such as NK cells and T cells, to neratinib. Thus, to modulate or terminate the treatment, further administration of neratinib to which said cells have been made sensitive may be performed in order to deplete in vivo said cells.

Said method can be used to produce engineered cells for treating cancer, infection or immune disease in a patient by unique or sequential administration thereof to a patient.

As a preferred embodiment, the invention provides the administration of an immune cell made hypersensitive to neratinib drug by inactivating of the gene encoding AMPD3, said cell being further engineered to endow a chimeric antigen receptor (CAR) against said cancerous cell, infectious agent or dysfunctioning host immune cell.

The engineered cells according to the present invention can advantageously combine a first gene inactivation into a gene encoding AMPD3 to confer hypersensitivity to neratinib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the AMPD3 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding AMPD3 to confer hypersensitivity to neratinib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding AMPD3 to confer hypersensitivity to neratinib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding AMPD3 to confer hypersensitivity to neratinib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding AMPD3 to confer hypersensitivity to neratinib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of NR1H2 Expression to Confer Hypersensitivity to Neratinib

According to a preferred embodiment, the present invention provides a method of producing human cells that may be depleted in-vivo as part of a cell therapy treatment, said method comprising:

(a) Providing human cells;
(b) Ex-vivo inducing neratinib specific hypersensitivity into said human cell by selectively inhibiting the expression of a gene encoding NR1H2, and
(c) Optionally assaying the hypersensitivity of said human cell engineered in step b) to said drug;
(d) Culturing, and preferably expanding, the engineered immune cells obtained in step b).

NR1H2 enzyme has RefSeq P55055 and is encoded by the gene under reference NM_007121. This enzyme regulates cholesterol uptake through MYLIP-dependent ubiquitination of LDLR, VLDLR and LRP8; DLDLR and LRP8. It exhibits a ligand-dependent transcriptional activation activity (Sakurabashi A. et al, 2015, J. Steroid Biochem. Mol. Biol. 149:80-88).

According to a preferred embodiment, said human NR1H2 inhibition is performed by a least one rare-cutting endonuclease directed against a target sequence comprised into the NCBI Reference Sequence RefSeq NM_007121.

According to a more preferred embodiment, said human NR1H2 inhibition is performed by a least one rare-cutting endonuclease targeting a polynucleotide sequence comprised into a sequence having at least 80%, preferably 90%, more preferably 95% and mostly preferably 99% identity with SEQ ID NO. 20.

According to a preferred embodiment, the immune cells according to the present invention, which expression of NR1H2 is inhibited, are administered to the patient prior to their elimination by the drug neratinib. Inhibition or inactivation of NR1H2 has been found by the inventors to confer sensitivity of cells derived from lymphoid progenitor cells, such as NK cells and T cells, to neratinib. Thus, to modulate or terminate the treatment, further administration of neratinib to which said cells have been made sensitive may be performed in order to deplete in vivo said cells.

Said method can be used to produce engineered cells for treating cancer, infection or immune disease in a patient by unique or sequential administration thereof to a patient.

As a preferred embodiment, the invention provides the administration of an immune cell made hypersensitive to neratinib drug by inactivating of the gene encoding NR1H2, said cell being further engineered to endow a chimeric antigen receptor (CAR) against said cancerous cell, infectious agent or dysfunctioning host immune cell.

The engineered cells according to the present invention can advantageously combine a first gene inactivation into a gene encoding NR1H2 to confer hypersensitivity to neratinib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the NR1H2 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding NR1H2 to confer hypersensitivity to neratinib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding NR1H2 to confer hypersensitivity to neratinib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding NR1H2 to confer hypersensitivity to neratinib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding NR1H2 to confer hypersensitivity to neratinib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

Inhibition of CACNG5 to Confer Hypersensitivity to Neratinib

According to a preferred embodiment, the present invention provides a method of producing human cells that may be depleted in-vivo as part of a cell therapy treatment, said method comprising:
  (a) Providing human cells;
  (b) Ex-vivo inducing neratinib specific hypersensitivity into said human cell by selectively inhibiting the expression of a gene encoding CACNG5, and
  (c) Optionally assaying the hypersensitivity of said human cell engineered in step b) to said drug;
  (d) Culturing, and preferably expanding, the engineered immune cells obtained in step b).

Human CACNG5 protein (UniProt: Q9UF02) is a type II transmembrane AMPA receptor regulatory protein (TARP). TARPs regulate both trafficking and channel gating of the AMPA receptors (Burgess D L et al, 1999, Genome Res. 9(12):1204-13).

According to a preferred embodiment, said human CACNG5 inhibition is performed by a least one rare-cutting endonuclease directed against a target sequence comprised into the NCBI Reference Sequence RefSeq NM_145811.

According to a more preferred embodiment, said human CACNG5 inhibition is performed by a least one rare-cutting endonuclease targeting a polynucleotide sequence comprised into a sequence having at least 80%, preferably 90%, more preferably 95% and mostly preferably 99% identity with SEQ ID NO. 12 or NO. 13.

According to a preferred embodiment, the immune cells according to the present invention, which expression of CACNG5 is inhibited, are administered to the patient prior to their elimination by the drug neratinib. Inhibition or inactivation of CACNG5 has been found by the inventors to confer sensitivity of cells derived from lymphoid progenitor cells, such as NK cells and T cells, to neratinib. Thus, to modulate or terminate the treatment, further administration of neratinib to which said cells have been made sensitive may be performed in order to deplete in vivo said cells.

Said method can be used to produce engineered cells for treating cancer, infection or immune disease in a patient by unique or sequential administration thereof to a patient.

As a preferred embodiment, the invention provides the administration of an immune cell made hypersensitive to neratinib drug by inactivating of the gene encoding CACNG5, said cell being further engineered to endow a chimeric antigen receptor (CAR) against said cancerous cell, infectious agent or dysfunctioning host immune cell.

The engineered cells according to the present invention can advantageously combine a first gene inactivation into a gene encoding CACNG5 to confer hypersensitivity to neratinib and a further genetic engineering to confer specific resistance to another drug, such additional modification may be performed by a gene inactivation or by gene overexpression for instance of a mutant form of a gene, said gene being involved in the metabolization of said drug.

In particular, said further genetic engineered of cells according to the present invention, in addition to the CACNG5 inhibition or inactivation, confers resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, said engineered cells of the present invention can advantageously combine a first gene inactivation into a gene encoding CACNG5 to confer hypersensitivity to neratinib and said further genetic engineering is a gene inactivation of a gene selected in the group of deoxycytidine kinase (dCk), hypoxanthine guanine phosphoribosyl transferase (HPRT), glucocorticoid receptor (GR) and CD52, conferring specific drug resistance to purine nucleoside analogues (PNAs)—such as clofarabine or fludarabine—, corticosteroids, alemtuzumab respectively.

In another particular embodiment, said engineered cells of the present invention can advantageously combine a first gene inactivation into a gene encoding CACNG5 to confer hypersensitivity to neratinib and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding CACNG5 to confer hypersensitivity to neratinib and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding CACNG5 to confer hypersensitivity to neratinib and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

According to another embodiment of the present invention the expression of at least two genes selected in the group consisting of those encoding for CXCR3, NR1H2, URG4, PARP14, AMPD3, CCDC38, NFU1 or CACNG5 protein can be inhibited to confer higher hypersensitivity to neratinib.

In one embodiment, for all the above described cases when at least one gene selected in the group consisting of CXCR3, NR1H2, URG4, PARP14, AMPD3, CCDC38, NFU1 or CACNG5 is inactivated in the engineered cell administrated to the patient, the dose range of neratinib administrated subsequently to the patient is typically between 120 and 300 mg, advantageously between 150 and 240 mg of neratinib, preferably by oral administration.

Inhibition of SAMHD1 to Confer Hypersensitivity to Deoxycytidine Analogs

SAMDH1 (SAM domain and HD domain-containing protein 1) encodes a protein (UniProt: Q9Y3Z3), which is an enzyme that exhibits phosphohydrolase activity converting deoxynucleoside triphosphates (dNTPs) to inorganic phosphate (iPPP) and a 2'-deoxynucleoside (i.e. deoxynucleosides without a phosphate group). It more particularly catalyzes hydrolyzation of deoxycytidine analogs, in particular cyctostatic deoxycytidine analog cytarabine (Ara-c).

AraC (cytarabine) is the most active deoxycytidine analog agent available against acute myelogenous leukemia (AML). In AML, both the cytotoxicity of Ara-C in-vitro and the clinical response to Ara-C therapy are correlated with the ability of AML blasts to accumulate the active metabolite Ara-C triphosphate (Ara-CTP) which causes DNA damage through perturbation of DNA synthesis [Kufe et al. (1984) Relationships among Ara-CTP pools formation of Ara-C DNA and cytotoxicity of human leukemic cells. *Blood.* 64:54-58]. The inventors have successfully pursued the idea of transposing the mechanism observed in tumor cells into healthy primary cells According to a preferred embodiment, the present invention provides a method of producing human cells that may be depleted in-vivo as part of a cell therapy treatment, said method comprising:

(a) Providing human cells;
(b) Ex-vivo inducing deoxycytidine analogs hypersensitivity into said human cell by selectively inhibiting the expression of a gene encoding SAMHD1, and
(c) Optionally assaying the hypersensitivity of said human cell engineered in step b) to a deoxycytidine analogs drug;
(d) Culturing, and preferably expanding, the engineered immune cells obtained in step b).

Such hypersensitivity could be generated by genetic inactivation of some other specific genes that are directly or indirectly involved in the compound metabolization pathway, which SAMDH1 belongs to. As a result, the cells cannot metabolize (detoxify) deoxycytidine analogs into non active compounds.

SAMHD1 is expressed over a wide variety of cell type including T-cells. Thus, the inhibition or inactivation of the expression of SAMHD1 primary immune cells is particularly attractive to make those cells more sensitive to Purine Nucleotide Analogues, such as 1-B-D-arabinofuranosylcytosine (Ara-C), 5-aza-2'-deoxycytidine (DAZ) and Ara-5-azacytosine (AAC), Clofarabine or Fludarabine.

According to a preferred embodiment, human SAMHD1 inhibition is performed by a least one rare-cutting endonuclease directed against a target sequence comprised into the NCBI Reference Sequence RefSeq NM_015474.

According to a preferred embodiment, the resulting cells according to the present invention, which expression of SAMHD1 is inhibited, are administered to a patient at an effective concentration for obtaining a therapeutic effect and then are totally or partially depleted by using deoxycytidine analog(s), such as cytarabine. Inhibition or inactivation of SAMHD1 has been found to confer sensitivity to deoxycytidine analogs especially to cells derived from lymphoid progenitor cells, such as NK cells and T cells.

The method of the invention can be used to produce engineered cells for treating cancer, infection or immune disease in a patient by unique or sequential administration thereof to a patient.

As a preferred embodiment, the cells can be further engineered to endow a chimeric antigen receptor (CAR) directed against malignant or infected cells, infectious agent or dysfunctioning host immune cell or any undesirable cell type.

The engineered cells according to the present invention can advantageously combine a first gene inactivation into a gene encoding SAMHD1 to confer hypersensitivity to deoxycytidine analogs and a further genetic engineering to confer specific resistance to another drug, such additional modification may be performed by a gene inactivation or by gene overexpression for instance of a mutant form of a gene, said gene being involved in the metabolization of said other drug.

In particular, said further genetic engineered of cells according to the present invention, in addition to the SAMHD1 inhibition or inactivation, can confer resistance to a drug selected in the group consisting of alkylating agents (e.g., cyclophosphamide, ifosamide), metabolic antagonists (e.g., purine nucleoside antimetabolite such as clofarabine, fludarabine or 2'-deoxyadenosine, 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, immunomodulating agents such as thalidomide (Thalomid®) Lenalidomide (Revlimid®) Pomalidomide (Pomalyst®), proteasome inhibitors such as Bortezomib (Velcade®), Carfilzomib (Kyprolis®), Histone deacetylase (HDAC) inhibitors such as Panobinostat (Farydak®), or a therapeutic derivative of any thereof.

In a more particular embodiment, the engineered cells of the present invention can advantageously combine a first gene inactivation into a gene encoding SAMHD1 to confer hypersensitivity to deoxycytidine analogs and said further genetic engineering is a gene inactivation of a gene selected in the group: hypoxanthine guanine phosphoribosyl transferase (HPRT), glucocorticoid receptor (GR) or CD52.

In another particular embodiment, said engineered cells of the present invention can advantageously combine a first gene inactivation into a gene encoding SAMHD1 to confer hypersensitivity to deoxycytidine analogs and said further genetic engineering is an expression or overexpression of a gene involved in the metabolization of one or several specific drug(s), said latter gene expression or overexpression being of the wild type form or the mutant form depending of the considered gene.

As exemplary embodiments, said engineered cells of the present invention can combine a first gene inactivation into a gene encoding SAMHD1 to confer hypersensitivity to deoxycytidine analogs and said further genetic engineering is a gene expression of a mutated gene selected in the group consisting of dihydrofolate reductase (DHFR) inosine monophosphate dehydrogenase 2 (IMPDH2), calcineurin (PP2B) and methylguanine transferase (MGMT), conferring specific drug resistance to respectively anti-folate preferably methotrexate (MTX), to MPDH inhibitors such as mycophenolic acid (MPA) or its prodrug mycophenolate mofetil (MMF), to calcineurin inhibitor such as FK506 and/or Cs and to alkylating agents, such as nitrosoureas and temozolomide (TMZ).

The above mutated genes such as DHFR, IMPDH2, PP2B, MGMT can be obtained such as described in WO 2015075195.

As exemplary embodiments, said engineered cells of the present invention can combine a first gene inactivation into a gene encoding SAMHD1 to confer hypersensitivity to deoxycytidine analogs and said further genetic engineering is a gene expression of a wild type gene selected in the group consisting of MDR1, ble and mcrA, conferring specific drug resistance to respectively MDR1 resistance drugs such as 4-nitroquinoline-N-oxide, cerulenin, and brefeldin A, to bleomycin and to mitomycin C.

According to another embodiment of the present invention the expression of at least two genes selected in the group consisting of those encoding for CXCR3, NR1H2, URG4, PARP14, AMPD3, CCDC38, NFU1 or CACNG5 protein can be inhibited to confer higher hypersensitivity to deoxycytidine analogs.

According to the invention, the above engineered cells can be depleted preferably by using a EC50 dose range of Ara-CTP administrated subsequently to the patient between 50 and 350 nM, advantageously between 50 and 250 nM, more advantageously between 50 and 100 nM, Further Genetic Engineering by an Additional Gene Overexpression or by Gene Inhibition for Conferring Another Specific Drug Hypersensitivity The present invention relates to a method for producing a hypersensitive immune cell such as described above, wherein said human cell, preferably immune cell, is further engineered by inducing two drug hypersensitivities into said cell by selectively overexpressing (sequentially or simultaneously) two genes in its genome directly or indirectly involved in the metabolization, elimination or detoxification of two different drugs to which said cell is sensitive. An additional specific drug hypersensibility may be useful in case of cell escaping from the depletion to the first drug.

Thus, according to one alternative, the method of producing human cell that may be depleted in-vivo as part of a cell therapy comprises:

Providing an human cell, preferably human immune cell Inducing a drug hypersensitivity into said cell by selectively overexpressing at least one gene in its genome directly or indirectly involved in the metabolization, elimination or detoxification of a specific drug;

(a) Inducing an additional drug hypersensitivity into said cell by selectively inhibiting the expression of another gene in its genome directly or indirectly involved in the metabolization, elimination or detoxification of a drug which is different of that in step (b); said other gene being preferably selected in the group of GGH, RhoA, CDK5, CXCR3, NR1H2, URG4, PARP14, AMPD3, CCDC38, NFU1, CACNG5 and SAMHD1;

(b) Optionally assaying the hypersensitivity to said drug of the cell engineered in step (b) and/or (c);

(c) Culturing, and preferably expanding, the engineered immune cells obtained in step (c).

According to another alternative, the method of producing human cell that may be depleted in-vivo as part of a cell therapy comprises:

Providing a human cell, preferably human immune cell;

Inducing an drug hypersensitivity into said immune cell by selectively overexpressing at least one gene in its genome directly or indirectly involved in the metabolization, elimination or detoxification of a specific drug;

(a) Inducing an additional drug hypersensitivity into said cell by selectively inhibiting the expression of at least another directly or indirectly involved in the metabolization, elimination or detoxification of a specific drug which is different of that in step (b); said other gene being preferably selected in the group of GGH, RhoA, CDK5, CXCR3, NR1H2, URG4, PARP14, AMPD3, CCDC38, NFU1, CACNG5 and SAMHD1;

(b) Optionally assaying the hypersensitivity to said drug of the cell engineered in step (b) and/or (c);

(c) Culturing, and preferably expanding, the engineered immune cells obtained in step c).

In the two precedent embodiment, it is understood that step (c) may be performed before step (b).

Expression of Chimeric Antigen Receptor (CAR)

According to one embodiment, said human cells are human immune cells and are engineered by inhibiting or inactivating at least one gene to make them hypersensitive to a specific drug, and are further engineered to express a Chimeric Antigen Receptor (CAR).

By "chimeric antigen receptor" (CAR) it is meant a chimeric receptor which comprises an extracellular ligand-binding domain, a transmembrane domain and a signaling transducing domain. Chimeric Antigen Receptors (CAR) are able to redirect immune cell specificity and reactivity toward a selected target exploiting the ligand-binding domain properties. Said Chimeric Antigen Receptor combines a binding domain against a component present on the target cell, for example an antibody-based specificity for a desired antigen (e.g., tumor antigen) with a T-cell receptor-activating intracellular domain to generate a chimeric protein that exhibits a specific anti-target cellular immune activity. Generally, CAR consists of an extracellular single chain antibody (scFv) fused to the intracellular signaling domain of the T-cell antigen receptor complex zeta chain (scFv:ζ) and have the ability, when expressed in T-cells, to redirect antigen recognition based on the monoclonal antibody's specificity.

Thus, in another particular embodiment, the method further comprises a step of introducing into said lymphocytes a Chimeric Antigen Receptor.

The chimeric antigen receptors (CAR) of the present invention may be generated and characterized by using protocols such as those described in the part "general methods" of the Examples section.

Specific chimeric antigen receptors according to the invention can have different architectures, as they can be expressed, for instance, under a single-chain chimeric protein (scCAR) or under the form of several polypeptides (multi-chain CAR or mcCAR) including at least one such chimeric protein.

According to one embodiment, said chimeric antigen receptor which is expressed by immune cell is a CD123+, CD19+, CS1+, CD38+, ROR1+, CLL1+, hsp70+, CD22+, EGFRvIII+, BCMA+, CD33+, FLT3+, CD70+, WT1+, MUC16+, PRAME+, TSPAN10+, ROR1+, GD3+, CT83+ or mesothelin+.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

In a preferred embodiment, said extracellular ligand-binding domain comprises a single chain antibody fragment (scFv) comprising the light ($V_L$) and the heavy ($V_H$) variable fragment of a target antigen specific monoclonal antibody joined by a flexible linker.

The signal transducing domain or intracellular signaling domain of the CAR according to the present invention is responsible for intracellular signaling following the binding of extracellular ligand binding domain to the target resulting in the activation of the immune cell and immune response. Preferred examples of signal transducing domain for use in a CAR can be the cytoplasmic sequences of the T-cell receptor and co-receptors that act in concert to initiate signal transduction following antigen receptor engagement. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. In particular embodiment the signal transduction domain of the CAR of the present invention comprises a co-stimulatory signal molecule. A co-stimulatory molecule is a cell surface molecule other than an antigen receptor or their ligands that is required for an efficient immune response. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

The CAR according to the present invention is expressed on the surface membrane of the cell. Thus, the CAR can comprise a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can further comprise a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence.

Downregulation or mutation of target antigens is commonly observed in cancer cells, creating antigen-loss escape variants. Thus, to offset tumor escape and render immune cells more specific to target, the CD19 specific CAR can comprise another extracellular ligand-binding domains, to simultaneously bind different elements in target thereby augmenting immune cell activation and function. Examples of CD19 specific CAR are ScFv FMC63 (Kochenderfer J N, Wilson W H, Janik J E, et al. *Eradication of B-lineage cells and regression of lymphoma in a patient treated with autologous T cells genetically engineered to recognize CD19.* Blood 2010; 116(20):4099-410) or ScFv 4G7 CAR (described in the application filed under the number PCT/EP2014/059662). In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

In a preferred embodiment, said CAR which are expressed in the immune cell made drug-specific hypersensitive such as described earlier is chosen in the group consisting of anti-CD123 CAR, anti-CS1 CAR, anti-CD38 CAR, anti-CLL1 CAR, anti-Hsp70 CAR, anti-CD22, anti-EGFRvIII, anti-BCMA CAR, anti-CD33 CAR, anti-FLT3 CAR, anti-CD70 CAR, anti-WT1 CAR, anti-MUC16 CAR, anti-PRAME CAR, anti-TSPAN10 CAR, anti-ROR1 CAR, anti-GD3 CAR, anti-CT83 CAR and anti-mesothelin CAR.

In a preferred embodiment, said above CAR is single-chain CAR chosen in the group consisting of anti-CD123 single-chain CAR, anti-CS1 single-chain CAR, anti-CD38 single-chain CAR, anti-CLL1 single-chain CAR, anti-Hsp70 single-chain CAR, anti-EGFRvIII single-chain CAR, anti-BCMA single-chain CAR, anti-CD33 single-chain CAR, anti-FLT3 single-chain CAR, anti-CD70 single-chain CAR, anti-WT1 single-chain CAR, anti-MUC16 single-chain CAR, anti-PRAME single-chain CAR, anti-TSPAN10 single-chain CAR, anti-ROR1 single-chain CAR, anti-GD3 single-chain CAR, anti-CT83 single-chain CAR and mesothelin single-chain CAR;
  said CAR being expressed in an immune cell engineered to be made hypersensitive to a specific drug such as described previously has one of the polypeptide structure selected from V1, V3 or V5, as illustrated in FIG. 1;
  said structure comprising:
    an extra cellular ligand binding-domain comprising VH and VL from a monoclonal antibody selected in the group consisting of anti-CD123 mAb, anti-CS1 mAb, anti-CD38 mAb, anti-CLL1 mAb, anti-Hsp70 mAb, anti-EGFRvIII mAb, anti-BCMA mAb, anti-CD33 mAb, anti-FLT3 mAb, anti-CD70 mAb, anti-WT1 mAb, anti-MUC16 mAb, anti-PRAME mAb, anti-TSPAN10 mAb, anti-ROR1 mAb, anti-GD3 mAb, anti-CT83 mAb and anti-mesothelin mAb respectively;
    a hinge chosen in the group consisting of CD8alpha, FcERIII gamma and IgG1;
    a CD8a transmembrane domain;
    a cytoplasmic domain including a CD3 zeta signaling domain and;
    a 4-1BB co-stimulatory domain.

It is encompassed in the previous embodiment that the step of expression of CAR may be performed before the step of gene inhibition or gene inactivation to make cells drug-specific hypersensitive.

As some examples, VH and VL chains may be those described in the applications WO2015140268 for anti-CD123 scFv and WO2015121454 for anti-CS1 and anti-CD38 scFv.

All the other components chosen in the architecture of the CAR including transmembrane domain (i.e CD8αTM), co-stimulatory domain (ie. 4-1BB), hinge (CD8alpha, FcERIII gamma, IgG1), cytoplasmic signaling domain (ITAM CD3zeta) may be those already described, for instance, in the above cited WO2015140268 and WO2015121454 applications.

In another embodiment, said engineered immune cells which are made drug-specific hypersensitive such as previously disclosed are engineered to express a multi-chain CAR (mcCAR). By "multi-chain CARs", it is meant that the extracellular binding domain and the signaling domains are preferably located on different polypeptide chains, whereas co-stimulatory domains may be located on the same or a third polypeptide. Such multi-chain CARs can be derived from FcεRI (Ravetch et al, 1989), by replacing the high affinity IgE binding domain of FcεRI alpha chain by an extracellular ligand-binding domain such as scFv, whereas the N and/or C-termini tails of FcεRI beta and/or gamma chains are fused to signal transducing domains and co-stimulatory domains respectively. The extracellular ligand binding domain has the role of redirecting T-cell specificity towards cell targets, while the signal transducing domains activate or reduce the immune cell response. The fact that the different polypeptides derive from the alpha, beta and gamma polypeptides from FcεRI are transmembrane polypeptides sitting in juxtamembrane position provides a more flexible architecture to CARs, improving specificity towards the targeted molecule and reducing background activation of immune. Such multi-chain CAR architectures are disclosed in WO2014/039523, especially in FIGS. 2 to 4, and from page 14 to 21, which are herein incorporated by reference.

In a preferred embodiment, said above CAR is a multi-chain CAR chosen in the group consisting of anti-CD123 multi-chain CAR, anti-CS1 multi-chain CAR, anti-CD38 multi-chain CAR, anti-CLL1 multi-chain CAR, anti-Hsp70 multi-chain CAR, anti-CD22multi-chain CAR, anti-EGFRvIII multi-chain CAR, anti-BCMA multi-chain CAR, anti-CD33 multi-chain CAR, anti-FLT3 multi-chain CAR, anti-CD70 multi-chain CAR, anti-WT1 multi-chain CAR, anti-MUC16 multi-chain CAR, anti-PRAME multi-chain CAR, anti-TSPAN10 multi-chain CAR, anti-ROR1 multi-chain CAR, anti-GD3 multi-chain CAR, anti-CT83 multi-chain CAR and mesothelin multi-chain CAR.

In a preferred embodiment, said multi-chain CAR (mcCAR) which is expressed in an immune cell engineered to be made hypersensitive to a specific drug is an anti-CD123 mcCAR, anti-CS1 mcCAR, anti-CD38 mcCAR, anti-CLL1 mcCAR, anti-CD22 mcCAR or an anti-Hsp70 mc CAR.

Allogeneic Immune Cells and Process to Make them Allogeneic

The present invention relates also to allogeneic immunotherapy. Engraftment of allogeneic immune cells, in particular T-cells, is possible by inactivating at least one gene encoding a TCR component. TCR is rendered not functional in the cells by inactivating TCR alpha gene and/or TCR beta gene(s). TCR inactivation in allogeneic T-cells avoids GvHD. Such TCR inactivation can be performed according to WO2013176915, WO201575195, WO2015136001 or WO201575195.

According to a particular embodiment, said specific-drug-specific hypersensitive human cells, preferably human immune cells are further inactivated in their genes encoding TCRalpha or TCRbeta to make them allogeneic.

Consequently, according to another embodiment, the present invention relates to a method for making drug-hypersensitive human cells, preferably human immune cells, further engineered to render them allogeneic:
  (a) Providing a-cell;
  (b) Modifying said T-cell by inactivating at least one gene encoding a T-cell receptor (TCR) component;
  (c) Inducing a drug hypersensitivity into said cell by selectively inhibiting or inactivating the expression of at least one gene directly or indirectly involved in the metabolization, elimination or detoxification of said drug;
  (d) Culturing, and preferably expanding, said engineered T-cell in the presence of said drug.

It is encompassed in the previous embodiment that the step of gene inhibition or inactivation to confer drug-specific hypersensitivity may be performed before the step of TCR gene to make cells allogeneic.

Immune-Checkpoint Genes

It will be understood by those of ordinary skill in the art, that the term "immune checkpoints" means a group of molecules expressed by T-cells. These molecules effectively serve as "brakes" to down-modulate or inhibit an immune response. Immune checkpoint molecules include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as VSTM3, accession number: NM_173799), LAIR1 (also known as CD305, GenBank accession number: CR542051.1, (Meyaard, Adema et al. 1997)), SIGLEC10 (GeneBank accession number: AY358337.1), 2B4 (also known as CD244, accession number: NM_001166664.1), PPP2CA, PPP2CB, PTPN6, PTPN22, CD96, CRTAM, SIGLEC7 (Nicoll, Ni et al. 1999), SIGLEC9 (Zhang, Nicoll et al. 2000; Ikehara, Ikehara et al. 2004), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF (Quigley, Pereyra et al. 2010), GUCY1A2, GUCY1A3, GUCY1B2, GUCY1B3 which directly inhibit immune cells.

According to one particular embodiment, the present invention relates to the method for producing engineered drug-specific hypersensitive human cell, preferably human immune cell, said cell being engineered further to inactivate an immune-checkpoint gene.

The present invention relates particularly to a method of engineering allogeneic T-cell drug-specific hypersensitive, additionally being genetically modified to inactivate PD1 and/or CTLA-4.

Such immune checkpoint inactivation is preferably realized by expressing a rare-cutting endonuclease able to specifically cleave a target sequence within said immune checkpoint gene. In a preferred embodiment, said rare-cutting endonuclease is a TALE-nuclease. Such inactivation of immune checkpoint can be performed according to WO2014/184741.

Immunosuppressive Resistant T Cells

Allogeneic cells are rapidly rejected by the host immune system. It has been demonstrated that, allogeneic leukocytes present in non-irradiated blood products will persist for no more than 5 to 6 days (Boni, Muranski et al. 2008). Thus, to prevent rejection of allogeneic cells, the host's immune system has to be usually suppressed to some extent. However, in the case of adoptive immunotherapy the use of immunosuppressive drugs also have a detrimental effect on the introduced therapeutic T cells. Therefore, to effectively use an adoptive immunotherapy approach in these conditions, the introduced cells would need to be also resistant to the immunosuppressive treatment. Thus, in particular embodiment, the method according to the present invention further comprises a step of modifying T-cells to make them resistant immunosuppressive agent, preferably by inactivating at least one gene encoding a target for an immunosuppressive agent. An immunosuppressive agent is an agent that suppresses immune function by one of several mechanisms of action. In other words, an immunosuppressive agent is a role played by a compound which is exhibited by a capability to diminish the extent of an immune response. The method according to the invention allows conferring immunosuppressive resistance to T cells for immunotherapy by inactivating the target of the immunosuppressive agent in T cells. As non-limiting examples, targets for immunosuppressive agent can be a receptor for an immunosuppressive agent such as: CD52, glucocorticoid receptor (GR), a FKBP family gene member and a cyclophilin family gene member. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. Said rare-cutting endonuclease can be, for instance, a meganuclease, a Zinc finger nuclease or a TALE-nuclease. Such inactivation of a target of the immunosuppressive agent (ex: CD52) can be performed according to WO2013/176915.

The present invention thus encompasses embodiments, where cells are made resistant to a first drug by inactivating or reducing expression of a first gene as mentioned above, whereas said cells are rendered more sensitive to a second drug, preferably one selected among those suggested in this application, for their use in combination therapy with said first drug, while the second drug is being used for their optional depletion during the treatment.

Implementation of (Other) Suicide Genes

It may be desirable to further engineered immune cells, since engineered immune cells, in particular T-cells, can expand and persist for years after administration, to include another safety mechanism—in addition to the one based on the drug-hypersensitivity—to allow selective deletion of administrated T-cells. Thus, in some embodiments, the method of the invention can comprises the transformation of said T-cells with a recombinant suicide gene. Said recombinant suicide gene is used to reduce the risk of direct toxicity and/or uncontrolled proliferation of said T-cells once administrated in a subject (Quintarelli C, Vera F, blood 2007; Tey S K, Dotti G., Rooney C M, boil blood marrow transplant 2007). Suicide genes enable selective deletion of transformed cells in vivo. In particular, the suicide gene has the ability to convert a non-toxic pro-drug into cytotoxic drug or to express the toxic gene expression product. In other words, "Suicide gene" is a nucleic acid coding for a product, wherein the product causes cell death by itself or in the presence of other compounds. A representative example of such a suicide gene is one which codes for thymidine kinase of herpes simplex virus. Suicide genes also include as non-limiting examples caspase-9 or caspase-8. Caspase-9 can be activated using a specific chemical inducer of dimerization (CID). Suicide genes can also be polypeptides that are expressed at the surface of the cell and can make the cells sensitive to therapeutic monoclonal antibodies. As used herein "prodrug" means any compound useful in the methods of the present invention that can be converted to a toxic product. The prodrug is converted to a toxic product by the gene product of the suicide gene in the method of the present invention. A representative example of such a prodrug is ganciclovir which is converted in vivo to a toxic compound by HSV-thymidine kinase. The ganciclovir derivative subsequently is toxic to tumor cells. Other representative examples of prodrugs include acyclovir, FIAU [1-(2-deoxy-2-fluoro-β-D-arabinofuranosyl)-5-iodouracil] or 6-methoxypurine arabinoside for VZV-TK.

Delivery Methods

Polypeptides may be expressed in the cell as a result of the introduction of polynucleotides encoding said polypeptides into the cell. Alternatively, said polypeptides could be produced outside the cell and then introduced thereto.

The different methods described to make human cells, preferably immune cells, hypersensitive to a specific drug, involve the delivery of at least one polynucleotide construct, such as one encoding for a rare-cutting endonuclease which inactivates said drug-related gene, in particular one selected in the group consisting of GGH, RhoA, CDK5, CXCR3, NR1H2, URG4, PARP14, AMPD3, CCDC38, NFU1, CACNG5 and SAMHD1. Preferably, another polynucleotide encoding to a chimeric antigen receptor is delivered into drug-specific hypersensitive immune cells. Other(s) transgene(s) affecting diverse cell function such as drug resistance gene, C or suicide gene may be delivered. Such deliveries can be sequential—regardless of the order—or simultaneously.

As non-limiting example, said protein of interest such as endonuclease, chimeric antigen receptor, can be expressed in the cell by its introduction as a transgene preferably encoded by at least one plasmid vector.

Methods for introducing a polynucleotide construct into cells are known in the art and include as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells. Said plasmid vector can comprise a selection marker which provides for identification and/or selection of cells which received said vector. Different transgenes can be included in one vector. Said vector can comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

In a more preferred embodiment of the invention, polynucleotides encoding polypeptides such as rare-cutting endonuclease to confer drug-specific hypersensitivity and preferably a chimeric antigen receptor can be mRNA which is introduced directly into the cells, for example by electroporation. The inventors determined the optimal condition for mRNA electroporation in T-cell. The inventor used the cytoPulse technology which allows, by the use of pulsed electric fields, to transiently permeabilize living cells for delivery of material into the cells. The technology, based on the use of PulseAgile (BTX Havard Apparatus, 84 October Hill Road, Holliston, Mass. 01746, USA) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow exporting the polynucleotide into the cell.

Activation and Expansion of T-Cells

In one embodiment, said engineered drug-specific hypersensitive human cells in step d) of the above method of production are expanded in-vivo.

In one preferred embodiment, said engineered drug-specific hypersensitive d cells in step d) of the above method of production are expanded in vitro.

Whether prior to or after genetic modification of the cell (ie. T-cells), the latter can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T-cells can be expanded in vitro or in vivo. Generally, the T cells of the invention are expanded by contact with an agent that stimulates a CD3 TCR complex and a co-stimulatory molecule on the surface of the T-cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell. As non limiting examples, T-cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell.

Conditions appropriate for T-cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, IL-21 and TNF- or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T-cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics.

Therapeutic Applications

The present invention concerns methods of treatment using drug-specific hypersensitive human cells obtained by the method described earlier, in combination with its corresponding specific drug. This in vivo depletion is particularly adapted when a serious adverse event happens. Such adverse event may occur in case of allogeneic bone marrow transplantation when T cells were recognized as the central mediators of graft-versus-host disease (GVHD) or Cytokine release syndrome (CRS). Although the antigenic targets in adoptive T cell therapy are much better defined, the potential for adverse effects, both on-target and off-target, remains. Finally, other side events can cause an increase of liver enzymes, acute pulmonary infiltrates, B-cell depletion or hypogammaglobulinemia.

Drugs encompassed within the present invention are typically commonly used in the treatment of a wide range of cancers, including hematological malignancies (blood cancers, like leukemia and lymphoma), many types of carcinoma (solid tumors) and soft tissue sarcomas. The above cited drugs are approved ones by national health authorities or assayed in clinical trial. Doxorubicin is commonly used in the treatment of a wide range of cancers, including hematological malignancies (blood cancers, like leukemia and lymphoma), many types of carcinoma (solid tumors) and soft tissue sarcomas. It is often used in combination chemotherapy as a component of various chemotherapy regimens. Bortezomib, which corresponds to a derivate of boronic acid, is a therapeutic proteasome inhibitor. It has been tested in humans and approved in the U.S. for treating relapsed multiple myeloma and mantle cell lymphoma. Neratinib (HKI-272) is under investigation for the treatment of breast cancer and other solid tumors. Those drugs may be used in combination chemotherapy as a component of various chemotherapy regimens.

Cells that can be used with the disclosed methods are described in the previous section. Said treatment can be used to treat patients diagnosed with cancer, viral infection, autoimmune disorders. Cancers that may be treated include tumors that are not vascularized, or not yet substantially vascularized, as well as vascularized tumors. The cancers may comprise nonsolid tumors (such as hematological tumors, for example, leukemia and lymphomas) or may comprise solid tumors. Types of cancers to be treated with the allogeneic T-cell resistant to drugs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included. In an embodiment of the present invention, childhood acute lymphoblastic leukemia (ALL) and amyotrophic myeloma leukemia (AML) diseases are typically treated by allogeneic drug resistant T-cells according to the invention. This can be achieved by using drug resistant KO TRAC CD19+ CAR T-cells and drug resistant KO TRAC CD123+ T-cells respectively.

Said treatment can be ameliorating, curative or prophylactic. The invention is particularly suited for allogeneic immunotherapy, insofar as it enables the transformation of T-cells, typically obtained from donors, into non-alloreactive cells. This may be done under standard protocols and reproduced as many times as needed. The resulting modified T-cells are administrated to one or several patients, being made available as an "off the shelf" therapeutic product.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

In a general embodiment, the present invention relates to a method for treating cancer, infection or immune disease; wherein said human cell is an immune cell, preferably T cell, which is made hypersensitive to a specific drug and further engineered to endow a chimeric antigen receptor (CAR) by using the method such as described previously, said CAR being specific to a cell surface antigen of a cancerous cell, an infectious agent or a dysfunctioning host immune cell.

In particular, the present invention relates to methods of treatment of pathologies in human comprising the sequential administration to a patient in need of:
  at least one human cell made hypersensitive to at least one specific drug, preferably by inhibiting or inactivating at least one gene selected in the group consisting of GGH, RhoA, CDK5, CXCR3, NR1H2, URG4, PARP14, AMPD3, CCDC38, NFU1, CACNG5 and SAMHD1;
  at least one drug to which said immune cells is sensitive, preferably at least one selected in the group consisting of 5-FU, doxorubicin, bortezomid and neratinib, in order to deplete in vivo said immune cells in case of occurrence of an adverse event.

In a preferred embodiment, the method of treating cancer, infection or immune disease comprises a sequential administration to a patient of:
  at least one human cell which is a human immune cell made hypersensitive to 5-FU drug by inhibiting or inactivating GGH-encoding gene, preferably endowing a chimeric antigen receptor, said CAR being specific to a cell surface antigen of a cancerous cell, an infectious agent or a dysfunctioning host immune cell, and of;
  at least 5 FU drug to deplete in vivo said immune cells in case of occurrence of an adverse event.

In another preferred embodiment, the method of treating cancer, infection or immune disease comprises a sequential administration to a patient of:
  at least one human cell which is a human immune cell made hypersensitive to doxorubicin drug by inhibiting or inactivating RhoA-encoding gene, preferably endowing a chimeric antigen receptor, said CAR being specific to a cell surface antigen of a cancerous cell, an infectious agent or a dysfunctioning host immune cell, and of;
  at least doxorubicin drug to deplete in vivo said immune cells in case of occurrence of an adverse event.

In another preferred embodiment, the method of treating cancer, infection or immune disease comprises a sequential administration to a patient of:
  at least one human cell which is a human immune cell made hypersensitive to bortezomib drug by inhibiting or inactivating CDK5-encoding gene, preferably endowing a chimeric antigen receptor, said CAR being specific to a cell surface antigen of a cancerous cell, an infectious agent or a dysfunctioning host immune cell, and of;

at least bortezomib drug to deplete in vivo said immune cells in case of occurrence of an adverse event.

In another preferred embodiment, the method of treating cancer, infection or immune disease comprises a sequential administration to a patient of:
- at least one human cell which is a human immune cell made hypersensitive to neratinib drug by inhibiting or inactivating at least one gene in the group consisting of CXCR3, NR1H2, URG4, PARP14, AMPD3, CCDC38, NFU1 and CACNG5, said immune cell preferably endowing a chimeric antigen receptor, said CAR being specific to a cell surface antigen of a cancerous cell, an infectious agent or a dysfunctioning host immune cell, and of;
- at least neratinib drug to deplete in vivo said immune cells in case of occurrence of an adverse event.

In another preferred embodiment, the method of treating cancer, infection or immune disease comprises a sequential administration to a patient of:
- at least one human cell which is an immune cell made hypersensitive to 5-FU drug by inhibiting or inactivating GGH-encoding gene; said immune cell preferably endowing a chimeric antigen receptor, said CAR being specific to a cell surface antigen of a cancerous cell, an infectious agent or a dysfunctioning host immune cell
- methotrexate drug to which said engineered immune cell is resistant; said drug being used to treat cancerous cells sensitive to said drug; and of;
- at least 5 FU drug to which said immune cells is sensitive to deplete in vivo said immune cells in case of occurrence of an adverse event.

The administration of methotrexate and 5-FU may be sequential—any order considered—or simultaneous.

Doses of Drug to be Administered for Immune Cell Depletion

According to Otos R et al, 2011, values obtained from this in vitro test can be used to calculate the relationship between the in vitro drug concentrations and the in vivo ones. Typically, area under curve (AUC; area under the plasma, concentration curve versus time) values of the individual drugs can be used. For this comparison Quotient of Area Under Curve values ($QAUC^{72\ hr}$) are determined by the following formula: In vitro used concentration×72 hours (μg×hr/ml)/in vivo AUC72 hr (μg×h/ml). The in vivo $AUC^{72}_{hr}$ corresponds to the area under curve value achieved in patients under a 72 hours period. The in vivo $AUC^{72\ hr}$ was established from the clinical dose and half-time using the standard trapezoidal rule calculation.

The doses of drug to be used for depleting drug-hypersensitive engineered immune cells of the present invention have a value inferior or equal to those for which the Cmax is obtained, in order to minimize the probability of adverse events. The doses of each drug administrated for in vivo depleting engineered drug-hypersensitive human immune cell correspond essentially to the ones used in the clinical trials (clinicaltrial.com) and agreed by national health authorities.

Isolated Engineered Cell

One aspect of the present invention relates to human cell, preferably immune cell, which is engineered to have at least one gene inactivated, which is directly or indirectly involved in the metabolization, elimination or detoxification of a specific drug, to make this cell hypersensitive to said specific drug.

In particular, according to one embodiment, the drug-specific hypersensitive human cell is obtainable by the method of producing ex-vivo said immune cell which can be depleted in-vivo as part of a cell treatment, said method comprising:
(a) Providing said human cell;
(b) Inducing drug hypersensitivity into said human cell by selectively inhibiting the expression of at least one gene directly or indirectly involved in the metabolization, elimination or detoxification of said drug,
(c) Optionally assaying the hypersensitivity to said drug of the said human cell engineered in step b);
(d) Culturing, and preferably expanding, said engineered human cells obtained in step b).

Preferably, the present invention relates to human cell, preferably immune cell, which is engineered to have at least one gene inactivated, said gene being selected in the group consisting of GGH, RhoA, CDK5, CXCR3, NR1H2, URG4, PARP14, AMPD3, CCDC38, NFU1, CACNG5 and SAMHD1, which is directly or indirectly involved in the metabolization, elimination or detoxification of at least one selected in the group consisting of 5-FU (for GGH), doxorubicin (for RhoA), bortezomib (for CDK5), neratinib (for CXCR3, NR1H2, URG4, PARP14, AMPD3, CCDC38, NFU1 and CACNG5), and/or deoxycytidine analogs (for SAMHD1), to make this cell hypersensitive to said specific drug(s).

Preferably said human cell is a human immune cell such as T cell. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T-cell lines available and known to those skilled in the art, may be used. In another embodiment, said cell is preferably derived from a healthy donor. In another embodiment, said cell is part of a mixed population of cells which present different phenotypic characteristics.

According to a preferred embodiment, said human cell is CD8+ cell.

According to another preferred embodiment, said human cell is a primary cell.

Also, the present invention concerns an isolated human cell rendered sensitive to a drug obtainable by the method of production such as disclosed above.

According to another embodiment, an isolated drug-specific hypersensitive human cell, preferably immune cell is used as a medicament.

On one embodiment, said immune cells, such as T-cells of the invention can undergo robust in vivo expansion and can persist for an extended amount of time.

Administration of Engineered Human Cells

According to a preferred embodiment of the invention, said treatment is administrated into patients undergoing an immunosuppressive treatment. The present invention preferably relies on cells or population of cells, which have been made hypersensitive to at least one drug agent according to the present invention due to the inactivation of a drug specific metabolization-related gene. In this aspect, the drug treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, intracranially, by intravenous or intralymphatic injection, or intraperitoneally. In one embodiment, the cell compositions of the present invention are preferably administered by intravenous injection.

The administration of the cells or population of cells can consist of the administration of $10^3$-$10^{10}$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or pharmaceutical composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T-cells of the invention may be used in combination with chemotherapy, radiation, immunosuppressive agents, such as cyclosporin, azathioprine, mycophenolate, and FK506, antibodies, or other immunoablative agents such as CAMPATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T-cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded human cell, preferably immune cell, of the present invention. In an additional embodiment, expanded cells are administered before or following surgery.

The present invention relates to the use of at least one isolated human cell, preferably immune cell, that is sensitive to at least one drug such as described above, in sequential combination with to at least one drug to which said cell has been made sensitive, for a safer immunotherapy treatment.

Pharmaceutical Composition

The isolated drug specific hypersensitive human cells, preferably immune cells, and more preferably T-cells, of the present invention may be administered either alone, or as a pharmaceutical composition in combination with diluents and/or with other components such as IL-2 or other cytokines or cell populations.

Briefly, pharmaceutical compositions of the present invention may comprise T-cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g. aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The present invention is further drawn to methods for treating patients using the engineered cells previously described, in particular the following ones:

A method for transplanting human cells for the treatment of a pathology by sequential administration to a patient of:
  at least one human cell which is made hypersensitive to a specific drug by using the method according to the invention, and
  at least one drug to which said cells is sensitive to deplete in vivo said cells in case of occurrence of an adverse event.

A method for treating cancer, infection or immune disease in a patient by sequential administration to a patient of:
  at least one human cell which is a hematopoietic stem cell (HSC) and made hypersensitive to a specific drug by using the method according to the invention, and
  at least one drug to which said cells are sensitive to deplete in vivo said cells in case of occurrence of an adverse event.

A method according to the previous one, wherein said human cell is an immune cell, preferably T cell, which is made hypersensitive to a specific drug and further engineered to endow a chimeric antigen receptor (CAR) by using the method according to the invention, said CAR being specific to a cell surface antigen of a cancerous cell, an infectious agent or a dysfunctioning host immune cell.

A method of treatment by sequential administration to a patient of:
  at least one human cell which is an immune cell made hypersensitive to 5-FU drug by using the method of the invention, and of;

at least 5 FU drug to which said immune cells is sensitive to deplete in vivo said immune cells in case of occurrence of an adverse event.

A method of treatment by sequential administration to a patient of:
at least one human cell which is an immune cell made hypersensitive to doxorubicin drug by using the method according to the invention, and of;
at least doxorubicin drug to which said immune cells is sensitive to deplete in vivo said immune cells in case of occurrence of an adverse event.

A method of treatment by sequential administration to a patient of:
at least one human cell which is an immune cell made hypersensitive to bortezomib drug by using the method according to the invention and of;
at least 5 FU to which said immune cells is sensitive to deplete in vivo said immune cells in case of occurrence of an adverse event.

A method of treatment by sequential administration to a patient of:
at least one human cell which is an immune cell made hypersensitive to neratinib drug by using the method according to the invention and of;
at least neratinib drug to which said immune cells is sensitive to deplete in vivo said immune cells in case of occurrence of an adverse event.

A method of treatment by sequential administration to a patient of:
at least one human cell which is an immune cell made hypersensitive to 5-FU drug by using the method according to the invention;
at least 5 FU drug to which said immune cells is sensitive to deplete in vivo said immune cells in case of occurrence of an adverse event,
and wherein the patient is additionally treated for methotrexate-sensitive cancer by administration of methotrexate; said drug being used to treat cancerous cells sensitive to said drug.

Definitions

In the description above, a number of terms are used extensively. The following definitions are provided to facilitate understanding of the present embodiments.

Amino acid residues in a polypeptide sequence are designated herein according to the one-letter code, in which, for example, Q means Gln or Glutamine residue, R means Arg or Arginine residue and D means Asp or Aspartic acid residue.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

As used herein, "nucleic acid" or "nucleic acid molecule" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Nucleic acids can be either single stranded or double stranded.

By "gene" is meant the basic unit of heredity, consisting of a segment of DNA arranged in a linear manner along a chromosome, which codes for a specific protein or segment of protein, small RNA and the like. A gene typically includes a promoter, a 5' untranslated region, one or more coding sequences (exons), optionally introns, a 3' untranslated region. The gene may further comprise a terminator, enhancers and/or silencers.

The term "transgene" means a nucleic acid sequence (encoding, e.g. one or more polypeptides), which is partly or entirely heterologous, i.e. foreign, to the host cell into which it is introduced, or, is homologous to an endogenous gene of the host cell into which it is introduced, but which can be designed to be inserted, or can be inserted, into the cell genome in such a way as to alter the genome of the cell into which it is inserted (e.g. it is inserted at a location which differs from that of the natural gene or its insertion results in a knockout). A transgene can include one or more transcriptional regulatory sequences and any other nucleic acid, such as introns, that may be necessary for optimal expression of the selected nucleic acid encoding polypeptide. The polypeptide encoded by the transgene can be either not expressed, or expressed but not biologically active, in cells in which the transgene is inserted.

By "genome" it is meant the entire genetic material contained in a cell such as nuclear genome, chloroplastic genome, mitochondrial genome.

By "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from 10 to 45 base pairs (bp) in length, usually ranging from 10 to 35 base pairs in length. The endonuclease according to the present invention recognizes and cleaves nucleic acid at specific polynucleotide sequences, further referred to as "target sequence". The rare-cutting endonuclease can recognize and generate a single- or double-strand break at specific polynucleotides sequences.

In a particular embodiment, said rare-cutting endonuclease according to the present invention can be a Cas9 endonuclease. Indeed, recently a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the protospacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010). In the present invention, guide RNA can be designed for example to specifically target a gene encoding a TCR component. Following the pairing between the guide RNA and the target sequence, Cas9 induce a cleavage within TCR gene.

Rare-cutting endonuclease can also be a homing endonuclease, also known under the name of meganuclease. Such homing endonucleases are well-known to the art (Stoddard 2005). Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

Said rare-cutting endonuclease can be a modular DNA binding nuclease. By modular DNA binding nuclease is meant any fusion proteins comprising at least one catalytic domain of an endonuclease and at least one DNA binding domain or protein specifying a nucleic acid target sequence. The DNA binding domain is generally a RNA or DNA-binding domain formed by an independently folded polypeptide or protein domain that contains at least one motif that recognizes double- or single-stranded polynucleotides. Many such polypeptides have been described in the art having the ability to bind specific nucleic acid sequences. Such binding domains often comprise, as non limiting examples, helix-turn helix domains, leucine zipper domains, winged helix domains, helix-loop-helix domains, HMG-box domains, Immunoglobin domains, B3 domain or engineered zinc finger domain.

According to a preferred embodiment of the invention, the DNA binding domain is derived from a Transcription Activator like Effector (TALE), wherein sequence specificity is driven by a series of 33-35 amino acids repeats originating from *Xanthomonas* or *Ralstonia* bacterial proteins. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base ($T_O$) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence.

Other engineered DNA binding domains are modular base-per-base specific nucleic acid binding domains (MBBBD) (PCT/US2013/051783). Said MBBBD can be engineered, for instance, from the newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica* (Lackner, Moebius et al. 2011). MBBBD proteins comprise modules of about 31 to 33 amino acids that are base specific. These modules display less than 40% sequence identity with *Xanthomonas* TALE common repeats, whereas they present more polypeptides sequence variability. When they are assembled together, these modular polypeptides can although target specific nucleic acid sequences in a quite similar fashion as *Xanthomonas* TALE-nucleases. According to a preferred embodiment of the present invention, said DNA binding domain is an engineered MBBBD binding domain comprising between 10 and 30 modules, preferably between 16 and 20 modules. The different domains from the above proteins (modules, N and C-terminals) from *Burkholderia* and *Xanthomonas* are useful to engineer new proteins or scaffolds having binding properties to specific nucleic acid sequences. In particular, additional N-terminal and C-terminal domains of engineered MBBBD can be derived from natural TALE like AvrBs3, PthXo1, AvrHah1, PthA, Tal1c as non-limiting examples.

"TALE-nuclease" or "MBBBD-nuclease" refers to engineered proteins resulting from the fusion of a DNA binding domain typically derived from Transcription Activator like Effector proteins (TALE) or MBBBD binding domain, with an endonuclease catalytic domain. Such catalytic domain is preferably a nuclease domain and more preferably a domain having endonuclease activity, like for instance I-TevI, ColE7, NucA and Fok-I. In a particular embodiment, said nuclease is a monomeric TALE-Nuclease or MBBBD-nuclease. A monomeric Nuclease is a nuclease that does not require dimerization for specific recognition and cleavage, such as the fusions of engineered DNA binding domain with the catalytic domain of I-TevI described in WO2012138927. In another particular embodiment, said rare-cutting endonuclease is a dimeric TALE-nuclease or MBBBD-nuclease, preferably comprising a DNA binding domain fused to FokI. TALE-nuclease have been already described and used to stimulate gene targeting and gene modifications (Boch, Scholze et al. 2009; Moscou and Bogdanove 2009; Christian, Cermak et al. 2010). Such engineered TALE-nucleases are commercially available under the trade name TALEN® (Cellectis, 8 rue de la Croix Jarry, 75013 Paris, France).

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

The terms "vector" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

By "delivery vector" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomega-lovirus), and poxvirus (e. g. vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non-limiting example, that are able to integrate the genome of a target cell. At the opposite by "non-integrative lentiviral vectors (or NILV)" is meant efficient gene delivery vectors that do not integrate the genome of a target cell through the action of the virus integrase.

By cell or cells is intended any eukaryotic living cells, primary cells and cell lines derived from these organisms for in vitro cultures.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated;

«knockout» means that the gene is mutated to that extend it cannot be expressed;

"TRAC" refers to "T cell receptor alpha constant» and corresponds to TCRα subunit constant gene.

In addition to the preceding features, the invention comprises further features which will emerge from the following examples illustrating the method of engineering drug-specific hypersensitive T-cells for immunotherapy, as well as to the appended drawings.

General Methods

TALE-Nuclease-Mediated Inactivation of Drug Metabolization-Related Gene

To inactivate a gene such as one described here -GGH, RhoA, CDK5, CXCR3, NR1H2, URG4, PARP14, AMPD3, CCDC38, NFU1, CACNG5 and SAMHD1, two pairs of TALE-nucleases were designed for each gene, assembled and validated by sequencing (TALEN® were designed at Cellectis, 8 rue de la Croix Jarry and manufactured by Thermo Fisher Scientific, 81 Wyman Street, Waltham, Mass., U.S.A.). Once validated, mRNAs encoding the two TALE-nucleases were produced, polyadenylated and used to electroporate T cells using pulse agile technology (5 or 10 µg of TALE-nuclease mRNA left and right were used) such as described in the WO 2013/176915. A cold temperature shock are usually performed by incubating T cells at 30° C. immediately after electroporation and for 24 hours. A reactivation (12.5 µl beads/$10^6$ cells) was performed at D8 (8 days after the electroporation). The resulting T cells were allowed to grow and eventually characterized genotypically (by Endo T7 assay and deep sequencing at the gene loci to target) as well as phenotypically. Their phenotypical characterization consisted of (i), checking their ability to grow in the presence or absence of drug (ii), determining the $IC_{50}$ of corresponding drugs (such as PNAs, clofarabine and fludarabine, glucocorticoids), toward T cells and (iii), when a further gene inactivation is performed, determining the extent of such inactivation by FACS analysis.

Genotypic Characterization of T Cells Having Undergone a KO in a Drug Metaboliztion-Related Gene To assess the efficiency of drug metaboliztion-related gene inactivation, cells transfected with either 5 or 10 µg of TALE-nuclease mRNA were grown for 4 days (D4, 4 days after electroporation) and collected to perform T7 assays at the locus of interest. The T7 assay protocol is described in Reyon, D., Tsai, S. Q., Khayter, C., Foden, J. A., Sander, J. D., and Joung, J. K. (2012) FLASH assembly of TALE-nucleases for high-throughput genome editing. Nat Biotechnologies.

Determination of Growth Rate of T Cells with a KO in the Gene of Interest (GOI)

T cells with a GOI-KO are tested for their growth rate and for their reactivation with respect to WT cells.

Selection of GOI-KO T Cell in the Presence of the Drug

GOI KO or WT T cells are typically allowed to grow from D8 to D13 and then incubated with or without corresponding drug to which KO T cells are made resistant until D18. Cells were collected at D8 (before drug addition) and at D18 (after drug incubation) and were used to perform an endo T7 assay.

Determination of IC50 for the Drug on GOI KO T Cells Versus WT T Cells

To further investigate the ability of T cells to resist to the drug, IC50 for this drug was determined on GOI KO and WT T cells. The cells were collected 3 days after transfection were incubated for 2 days in media having different concentrations of said drug. At the end of drug incubation, viability of T cells was determined by FACS analysis.

Primary T-Cell Cultures

T cells were purified from Buffy coat samples provided by EFS (Etablissement Francais du Sang, Paris, France) using Ficoll gradient density medium. The PBMC layer was recovered and T cells were purified using a commercially available T-cell enrichment kit. Purified T cells were activated in X-Vivo™-15 medium (Lonza) supplemented with 20 ng/mL Human IL-2, 5% Human, and Dynabeads Human T activator CD3/CD28 at a bead:cell ratio 1:1 (Life Technologies).

CAR mRNA Transfection

Transfections are typically done at Day 4 or Day 11 after T-cell purification and activation. 5 millions of cells were transfected with 15 µg of mRNA encoding the different CAR constructs. CAR mRNAs are usually produced using T7 mRNA polymerase and transfectionsdone using Cytopulse technology, for instance by applying two 0.1 mS pulses at 3000V/cm followed by four 0.2 mS pulses at 325V/cm in 0.4 cm gap cuvettes in a final volume of 200 µl of "Cytoporation buffer T" (BTX Harvard Apparatus). Cells were immediately diluted in X-Vivo™-15 media and incubated at 37° C. with 5% $CO_2$. IL-2 was added 2 h after electroporation at 20 ng/mL.

T-Cell Transduction

Transduction of T-cells with recombinant lentiviral vectors expression the CAR are typically carried out three days after T-cell purification/activation. Lentiviral vectors were produced by Vectalys SA (Toulouse, France) by transfection of genomic and helper plasmids in HEK-293 cells. Transductions were carried out at a multiplicity of infection of 5, using $10^6$ cells per transduction. CAR detection at the surface of T-cells was done using a recombinant protein consisting on the fusion of the extracellular domain of the human protein such as CD123 or CD19 together with a murine IgG1 Fc fragment (produced by LakePharma). Binding of this protein to the CAR molecule was detected with a PE-conjugated secondary antibody (Jackson Immunoresearch) targeting the mouse Fc portion of the protein, and analyzed by flow cytometry.

Degranulation Assay (CD107a Mobilization)

T-cells were incubated in 96-well plates (40,000 cells/well), together with an equal amount of cells expressing various levels of the CD123 protein. Co-cultures were maintained in a final volume of 100 µl of X-Vivo™-15 medium (Lonza) for 6 hours at 37° C. with 5% $CO_2$. CD107a staining was done during cell stimulation, by the addition of a fluorescent anti-CD107a antibody at the beginning of the co-culture, together with 1 µg/ml of anti-CD49d, 1 µg/ml of anti-CD28, and 1× Monensin solution. After the 6 h incubation period, cells were stained with a fixable viability dye and fluorochrome-conjugated anti-CD8 and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection.

IFN Gamma Release Assay

T-cells were incubated in 96-well plates (40,000 cells/well), together with cell lines expressing various levels of the CD123 protein. Co-cultures were maintained in a final volume of 100 µl of X-Vivo™-15 medium (Lonza) for 24 hours at 37° C. with 5% $CO_2$. After this incubation period the plates were centrifuged at 1500 rpm for 5 minutes and the supernatants were recovered in a new plate. IFN gamma detection in the cell culture supernatants was done by ELISA assay. The IFN gamma release assays were carried by starting the cell co-cultures 24 h after mRNA transfection.

Cytotoxicity Assay

T-cells were incubated in 96-well plates (100,000 cells/well), together with 10,000 target cells (expressing the CAR-T cell target protein) and 10,000 control (not expressing the CAR-T cell target protein) cells in the same well. Target and control cells were labelled with fluorescent intracellular dyes (CFSE or Cell Trace Violet) before co-culturing them with CAR+ T-cells. The co-cultures were incubated for 4 hours at 37° C. with 5% $CO_2$. After this incubation period, cells were labelled with a fixable viability dye and analyzed by flow cytometry. Viability of each cellular population (target cells or control cells which do not express the targeted antigen surface protein) was determined and the % of specific cell lysis was calculated. Cytotoxicity assays were carried out 48 h after mRNA transfection.

T-Cell Transduction

Transduction of T-cells with recombinant lentiviral vectors expression the CAR is typically carried out three days after T-cell purification/activation. CAR detection at the surface of T-cells was done using a recombinant protein consisting on the fusion of the extracellular domain of the human targeted protein of interest, together with a murine IgG1 Fc fragment. Binding of this protein to the CAR molecule was detected with a fluorochrome-conjugated secondary antibody targeting the mouse Fc portion of the protein, and analyzed by flow cytometry.

Example 1: Engineering T Cell Hypersensitivity to Doxorubicin Drug

A constitutive genetic inactivation of RhoA is performed by site specific TALE-nuclease in exon 3 of RhoA (SEQ ID NO. 1) or in exon 1 of RhoA (SEQ ID NO. 2) to allow the generation of doxorubicin-hypersensitive T cells.

Example 2: Engineering T Cell Hypersensitivity to Bortezomib

A constitutive genetic inactivation of CDK5 is performed in T cells by using site specific TALE-nucleases in exon 2 (SEQ ID NO. 3 or SEQ ID NO. 4) or in exon 4 of CDK5 (SEQ ID NO. 5) to allow the generation of bortezomib-hypersensitive T cells.

Example 3: Engineering T Cell Hypersensitivity to Neratinib

The genes CXCR3, CCDC38, NFU1, CACNG5, NR1H, URG4, PARP14 and AMPD3 are indirectly linked to neratinib resistance. Downregulation of these genes in breast cancer cell lines was shown to increase their sensitivity to Neratinib (Seyhan A et al, 1989). A constitutive genetic inactivation of these genes is performed to enable the development of neratinib-hypersensitive T cells by site specific nucleases TALE-nucleases targeting respectively exon 2 of CXCR3 (SEQ ID NO. 6 or SEQ ID NO. 7), exon 2 or exon 3 of CCDC38 (SEQ ID NO. 8 or SEQ ID NO. 9), exon 2 of NFU1 (SEQ ID NO. 10 or SEQ ID NO. 11), exon 2 or exon 3 of CACGN5 (SEQ ID NO. 12 or SEQ ID NO. 13), exon 2 of NR1H2 (SEQ ID NO. 20), exon 2 or exon 3 of URG4 (SEQ ID NO. 18 or SEQ ID NO. 19), exon 1 or exon 3 of PARP14 (SEQ ID NO. 16 or SEQ ID NO. 17), exon 1, exon 2 or exon 3 of AMPD3 (SEQ ID NO. 21, SEQ ID NO. 22 or SEQ ID NO. 23).

Example 4: Engineering T Cell Hypersensitivity to GGH

A constitutive genetic inactivation of CDK5 is performed in T cells by using site specific nucleases TALE-nucleases targeting exon 2 or exon 3 of GGH1 (SEQ ID NO 14 and SEQ ID NO 15) to make them hypersensitive to 5FU and/or resistant to MTX.

TABLE 1

Polynucleotide sequences referred to in the examples

| SEQ ID NO. # | Description | Polynucleotide sequences |
|---|---|---|
| 1 | RhoA_EXON3 TALEN TARGET | TCTTTCAGAAAACATCCCAGAAA AGTGGACCCCAGAAGTCAAGCA |
| 2 | RhoA_EXON1 TALEN TARGET | TGGCAGATATCGAGGTGGATGGA AAGCAGGTGAGTATACTTTTCA |
| 3 | CDK5_EXON2 TALEN TARGET | TGACCTCCTTCCCCTAGGCACCT ACGGAACTGTGTTCAAGGCCAAA A |
| 4 | CDK5_EXON2 TALEN TARGET | TGACCTCCTTCCCCTAGGCACCT ACGGAACTGTGTTCAAGGCCA |
| 5 | CDK5_EXON4 TALEN TARGET | TTCTTTTGCCCTAGGCTTCATGA CGTCCTGCACAGCGACAAGAA |
| 6 | CXCR3_EXON2 TALEN TARGET | TTGGCTCTGGCCTCTGCAAAGTG GCAGGTGCCCTCTTCAACATCA |
| 7 | CXCR3_EXON2b TALEN TARGET | TGGCCTGCATCAGCTTTGACCGC TACCTGAACATAGTTCATGCCA |
| 8 | CCDC38_EXON2 TALEN TARGET | TTAACAGGTAAAGTAAAAGATGG CTCAACCAAAGAGGACAGGCCTT ATA |
| 9 | CCDC38_EXON3 TALEN TARGET | TCTACCAGAAAACTACTTTTTCA TCCAGAATGAAGAGTCATTCA |
| 10 | NFU1_EXON2 TALEN TARGET | TGCAGGTTCTGTCATATGTTGAA GAATCCATACACCATTAAGAA |
| 11 | NFU1_EXON2 TALEN TARGET | TACAAAGACCACTTTTCCCACTA CCTGCAGCCTTTTATCACCCA |
| 12 | CACGN5_EXON2 TALEN TARGET | TTCTTGTCTCCACAGGTGAGGAG CGGGGGCGTTGCTTCACCATAGA ATA |
| 13 | CACGN5_EXON3 TALEN TARGET | TTAATTAGAGATGATCCGCTCAG CCACACCATTCCCTCTGGTCA |
| 14 | GGH_EXON2 TALEN TARGET | TGTAAAGTACTTGGAGTCTGCAG GTGCGAGAGTTGTACCAGTAA |
| 15 | GGH_EXON3 TALEN TARGET | TTACAGAGAAAGACTATGAAATA CTTTTCAAATCTATTAATGGGTA |
| 16 | PARP14_Exon1 TALEN TARGET | TGAGTTGGTATGGCAAGGAAAAG GAACATTCAAGTTAACTGTCCA |
| 17 | PARP14_Exon3 TALEN TARGET | TTGGATACAAAACTCCCTCTTGA TGGTGGATTAGACAAAATGGAA |
| 18 | URG4_Exon_2 TALEN TARGET | TCCATAGATGGTACAAATGAGGC TCAGGACAATGATTTTCCAACA |
| 19 | URG4_Exon_3 TALEN TARGET | TGTCACTTTTGGGCCTAGAGACG TACCAGGTCCAGAAACTCAGCCT CCA |
| 20 | NR1h2_Exon_2 TALEN TARGET | TTCCAGGAAATGGCCCCCCTCAG CCTGGCGCCCCTTCTTCTTCACC CA |
| 21 | AMPD3_Exon_1 TALEN TARGET | TGAAGTGGATGAGCAAGTCCGGC TCCTGGCGGAGAAGGTGTTTGCT AAA |
| 22 | AMPD3_Exon_2 TALEN TARGET | TGGTCACTGGAGCCACTTCCCTG CCCACGCCAGCACCCTATGCCA |
| 23 | AMPD3_Exon_3 TALEN TARGET | TTGGAGGACTATGAGCAGGCAGC CAAGAGTCTGGCCAAGGCCCTA |

REFERENCES

Betts, M. R., J. M. Brenchley, et al. (2003). "Sensitive and viable identification of antigen-specific CD8+ T cells by a flow cytometric assay for degranulation." J Immunol Methods 281(1-2): 65-78.

Boch, J., H. Scholze, et al. (2009). "Breaking the code of DNA binding specificity of TAL-type III effectors." Science 326(5959): 1509-12.

Cermak, T., E. L. Doyle, et al. (2011). "Efficient design and assembly of custom TALEN and other TAL effector-based constructs for DNA targeting." Nucleic Acids Res 39(12): e82.

Christian, M., T. Cermak, et al. (2010). "Targeting DNA double-strand breaks with TAL effector nucleases." Genetics 186(2): 757-61.

Cong, L., F. A. Ran, et al. (2013). "Multiplex genome engineering using CRISPR/Cas systems." Science 339 (6121): 819-23.

Critchlow, S. E. and S. P. Jackson (1998). "DNA end-joining: from yeast to man." Trends Biochem Sci 23(10): 394-8.

Deltcheva, E., K. Chylinski, et al. (2011). "CRISPR RNA maturation by trans-encoded small RNA and host factor RNase III." Nature 471(7340): 602-7.

Deng, D., C. Yan, et al. (2012). "Structural basis for sequence-specific recognition of DNA by TAL effectors." Science 335(6069): 720-3.

Doublier S, Riganti C, Voena C, Costamagna C, Aldieri E, Pescarmona G, Ghigo D, Bosia A. 2008 "RhoA silencing reverts the resistance to doxorubicin in human colon cancer cells", Mol Cancer Res. 10:1607-2

Garneau, J. E., M. E. Dupuis, et al. (2010). "The CRISPR/Cas bacterial immune system cleaves bacteriophage and plasmid DNA." Nature 468(7320): 67-71.

Gasiunas, G., R. Barrangou, et al. (2012). "Cas9-crRNA ribonucleoprotein complex mediates specific DNA cleavage for adaptive immunity in bacteria." Proc Natl Acad Sci USA 109(39): E2579-86.

Geissler, R., H. Scholze, et al. (2011). "Transcriptional activators of human genes with programmable DNA-specificity." PLoS One 6(5): e19509.

Huang, P., A. Xiao, et al. (2011). "Heritable gene targeting in zebrafish using customized TALENs." Nat Biotechnol 29(8): 699-700.

Ikehara, Y., S. K. Ikehara, et al. (2004). "Negative regulation of T cell receptor signaling by Siglec-7 (p70/AIRM) and Siglec-9." J Biol Chem 279(41): 43117-25.

Jena, B., G. Dotti, et al. (2010). "Redirecting T-cell specificity by introducing a tumor-specific chimeric antigen receptor." Blood 116(7): 1035-44.

Jinek, M., K. Chylinski, et al. (2012). "A programmable dual-RNA-guided DNA endonuclease in adaptive bacterial immunity." Science 337(6096): 816-21.

Jonnalagadda, M., C. E. Brown, et al. (2013). "Engineering human T cells for resistance to methotrexate and mycophenolate mofetil as an in vivo cell selection strategy." PLoS One 8(6): e65519.

Kim S E, Cole P D, Cho R C, Ly A, Ishiguro L, Sohn K J, Croxford R, Kamen B A, Kim Y I, 2013 "γ-Glutamyl hydrolase modulation and folate influence chemosensitivity of cancer cells to 5-fluorouracil and methotrexate" Br J Cancer. 109(8):2175-88.

Li, L., M. J. Piatek, et al. (2012). "Rapid and highly efficient construction of TALE-based transcriptional regulators and nucleases for genome modification." Plant Mol Biol 78(4-5): 407-16.

Li, T., S. Huang, et al. (2011). "Modularly assembled designer TAL effector nucleases for targeted gene knockout and gene replacement in eukaryotes." Nucleic Acids Res 39(14): 6315-25.

Mahfouz, M. M., L. Li, et al. (2012). "Targeted transcriptional repression using a chimeric TALE-SRDX repressor protein." Plant Mol Biol 78(3): 311-21.

Mahfouz, M. M., L. Li, et al. (2011). "De novo-engineered transcription activator-like effector (TALE) hybrid nuclease with novel DNA binding specificity creates double-strand breaks." Proc Natl Acad Sci USA 108(6): 2623-8.

Mali, P., L. Yang, et al. (2013). "RNA-guided human genome engineering via Cas9." Science 339(6121): 823-6.

Meyaard, L., G. J. Adema, et al. (1997). "LAIR-1, a novel inhibitory receptor expressed on human mononuclear leukocytes." Immunity 7(2): 283-90.

Miller, J. C., S. Tan, et al. (2011). "A TALE nuclease architecture for efficient genome editing." Nat Biotechnol 29(2): 143-8.

Morbitzer, R., P. Romer, et al. (2011). "Regulation of selected genome loci using de novo-engineered transcription activator-like effector (TALE)-type transcription factors." Proc Natl Acad Sci USA 107(50): 21617-22.

Moscou, M. J. and A. J. Bogdanove (2009). "A simple cipher governs DNA recognition by TAL effectors." Science 326(5959): 1501.

Mussolino, C., R. Morbitzer, et al. (2011). "A novel TALE nuclease scaffold enables high genome editing activity in combination with low toxicity." Nucleic Acids Res 39(21): 9283-93.

Nicoll, G., J. Ni, et al. (1999). "Identification and characterization of a novel siglec, siglec-7, expressed by human natural killer cells and monocytes." J Biol Chem 274(48): 34089-95.

Park, T. S., S. A. Rosenberg, et al. (2011). "Treating cancer with genetically engineered T cells." Trends Biotechnol 29(11): 550-7.

Quigley, M., F. Pereyra, et al. (2010). "Transcriptional analysis of HIV-specific CD8+ T cells shows that PD-1 inhibits T cell function by upregulating BATF." Nat Med 16(10): 1147-51.

Sakamoto E, Tsukioka S, Oie S, Kobunai T, Tsujimoto H, Sakamoto K, Okayama Y, Sugimoto Y, Oka T, Fukushima M, Oka T, 2008, "Folylpolyglutamate synthase and gamma-glutamyl hydrolase regulate leucovorin-enhanced 5-fluorouracil anticancer activity" Biochem Biophys Res Commun. 365(4):801-7.

Sander, J. D., L. Cade, et al. (2011). "Targeted gene disruption in somatic zebrafish cells using engineered TALENs." Nat Biotechnol 29(8): 697-8.

Sorek, R., C. M. Lawrence, et al. (2013). "CRISPR-mediated Adaptive Immune Systems in Bacteria and Archaea." Annu Rev Biochem.

Stoddard, B. L. (2005). "Homing endonuclease structure and function." Q Rev Biophys 38(1): 49-95.

Sugimoto, Y., S. Tsukahara, et al. (2003). "Drug-selected co-expression of P-glycoprotein and gp91 in vivo from an MDR1-bicistronic retrovirus vector Ha-MDR-IRES-gp91." J Gene Med 5(5): 366-76.

Takebe, N., S. C. Zhao, et al. (2001). "Generation of dual resistance to 4-hydroperoxycyclophosphamide and methotrexate by retroviral transfer of the human aldehyde dehydrogenase class 1 gene and a mutated dihydrofolate reductase gene." Mol Ther 3(1): 88-96.

Tesson, L., C. Usal, et al. (2011). "Knockout rats generated by embryo microinjection of TALENs." Nat Biotechnol 29(8): 695-6.

Weber, E., R. Gruetzner, et al. (2011). "Assembly of designer TAL effectors by Golden Gate cloning." PLoS One 6(5): e19722.

Yam, P., M. Jensen, et al. (2006). "Ex vivo selection and expansion of cells based on expression of a mutated inosine monophosphate dehydrogenase 2 after HIV vector transduction: effects on lymphocytes, monocytes, and CD34+ stem cells." Mol Ther 14(2): 236-44.

Zhang, F., L. Cong, et al. (2011). "Efficient construction of sequence-specific TAL effectors for modulating mammalian transcription." Nat Biotechnol 29(2): 149-53.

Zhang, J. Q., G. Nicoll, et al. (2000). "Siglec-9, a novel sialic acid binding member of the immunoglobulin superfamily expressed broadly on human blood leukocytes." J Biol Chem 275(29): 22121-6.

The invention claimed is:

1. A method of producing human immune cells having drug hypersensitivity, said method comprising: (a) providing human immune cells: (b) inducing drug hypersensitivity in said human cell by selectively cleaving a gene selected from GGH, RhoA, CDK5, CXCR3, NR1 H2, URG4, PARP14, AMPD3, CCDC38, NFU1 and CACNG5 with at least one rare-cutting endonuclease or targeted nickase targeting said gene, wherein the wherein a rare-cutting endonuclease or targeted nickase targets a sequence selected from: SEQ ID NO:14, or a sequence having at least 95% identity with SEQ ID NO:15; SEQ ID NO:1, or a sequence having at least 95% identity with SEQ ID NO:2; SEQ ID NO:3, or a sequence having at least 95% identity with SEQ ID NO:4; and SEQ ID NO:6-11, 18-19,16-17, 21-23, 20 and 12-13, or a sequence having at least 95% identity with the SEQ ID NO:6-11, 18-19, 16-17, 21-23, 20 and 12-13; (c) selecting for hypersensitivity to said drug of the human cell engineered in step b); and (d) expanding the selected engineered immune cells obtained in step c).

2. The method of claim 1, wherein said human immune cells are human hematopoietic stem cells (hHSC).

3. The method of claim 1, wherein said human immune cells are human primary cells.

4. The method of claim 3, wherein said human primary cells are T cells.

5. The method of claim 1, wherein said cleavage is obtained by introducing into said human immune cell at least one rare-cutting endonuclease or targeted nickase targeting said gene.

6. The method of claim 1, wherein said rare-cutting endonuclease is a TALE-nuclease.

7. The method of claim 1, wherein said rare-cutting endonuclease is an RNA-guided endonuclease.

8. The method of claim 1, wherein the GGH gene is cleaved conferring hypersensitivity to 5-FU and resistance to methotrexate.

9. The method of claim 8, wherein a rare-cutting endonuclease targets a sequence of SEQ ID NO:14, or a sequence having at least 95% identity with SEQ ID NO:15.

10. The method of claim 1, wherein the RhoA gene is cleaved conferring hypersensitivity to doxorubicin.

11. The method of claim 10, wherein a rare-cutting endonuclease targets a sequence of SEQ ID NO:1, or to a sequence having at least 95% identity with SEQ ID NO:2.

12. The method of claim 1, wherein the CDK5 gene is cleaved conferring hypersensitivity to bortezomib.

13. The method of claim 12, wherein a rare-cutting endonuclease targets a sequence of SEQ ID NO:3, or a sequence having at least 95% identity with SEQ ID NO:4.

14. The method of claim 1, wherein the gene selected in the group consisting of CXCR3, NR1H2, URG4, PARP14, AMPD3, CCDC38, NFU1 and CACNG5 is cleaved and confers hypersensitivity to neratinib.

15. The method of claim 14, wherein a rare-cutting endonuclease targets a sequence of SEQ ID NO:6-11, 18-19, 16-17, 21-23, 20 and 12-13, respectively, or a sequence having at least 95% identity with the SEQ ID NO:6-11, 18-19, 16-17, 21-23, 20 and 12-13.

16. The method of claim 1, wherein said immune cell expresses a Chimeric Antigen Receptor (CAR).

17. The method of claim 16, wherein said chimeric antigen receptor is directed against CD123, CD19, CS1, CD38, ROR11, CLL1, hsp70, CD22, EGFRvIII, BCMA, CD33, FLT3, CD70, WT1, MUC16, PRAME, TSPAN10, ROR1, GD3+, CT83, or mesothelin.

18. The method of claim 1, wherein said engineered cells in step d) are expanded in-vivo.

19. The method of claim 1, wherein said engineered cells in step d) are expanded in-vitro.

20. The method of claim 1, wherein said immune cells are further inactivated in their genes encoding TCRalpha or TCRbeta, to make them less alloreactive.

21. The method of claim 1, further comprising inactivating an immune-checkpoint gene.

* * * * *

UNITED STATES PATENT AND TRADEMARK OFFICE
CERTIFICATE OF CORRECTION

PATENT NO. : 10,894,093 B2
APPLICATION NO. : 16/092417
DATED : January 19, 2021
INVENTOR(S) : Valton et al.

Page 1 of 1

It is certified that error appears in the above-identified patent and that said Letters Patent is hereby corrected as shown below:

In the Claims

Column 67
Line 54, Claim 1, replace "wherein the wherein a" with "wherein the".

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*

```
                        SEQUENCE LISTING

<160> NUMBER OF SEQ ID NOS: 23

<210> SEQ ID NO 1
<211> LENGTH: 45
<212> TYPE: DNA
<213> ORGANISM: homo sapiens
<220> FEATURE:
<223> OTHER INFORMATION: RhoA_EXON3 TALEN TARGET

<400> SEQUENCE: 1
tctttcagaa aacatcccag aaaagtggac cccagaagtc aagca           45

<210> SEQ ID NO 2
<211> LENGTH: 45
<212> TYPE: DNA
<213> ORGANISM: homo sapiens
<220> FEATURE:
<223> OTHER INFORMATION: RhoA_EXON1 TALEN TARGET

<400> SEQUENCE: 2
tggcagatat cgaggtggat ggaaagcagg tgagtatact tttca           45

<210> SEQ ID NO 3
<211> LENGTH: 47
<212> TYPE: DNA
<213> ORGANISM: homo sapiens
<220> FEATURE:
<223> OTHER INFORMATION: CDK5_EXON2 TALEN TARGET

<400> SEQUENCE: 3
tgacctcctt cccctaggca cctacggaac tgtgttcaag gccaaaa         47

<210> SEQ ID NO 4
<211> LENGTH: 44
<212> TYPE: DNA
<213> ORGANISM: homo sapiens
<220> FEATURE:
<223> OTHER INFORMATION: CDK5_EXON2 TALEN TARGET

<400> SEQUENCE: 4
tgacctcctt cccctaggca cctacggaac tgtgttcaag gcca            44

<210> SEQ ID NO 5
<211> LENGTH: 44
<212> TYPE: DNA
<213> ORGANISM: homo sapiens
<220> FEATURE:
<223> OTHER INFORMATION: CDK5_EXON4 TALEN TARGET

<400> SEQUENCE: 5
ttcttttgcc ctaggcttca tgacgtcctg cacagcgaca agaa            44

<210> SEQ ID NO 6
<211> LENGTH: 45
<212> TYPE: DNA
<213> ORGANISM: homo sapiens
```

```
<220> FEATURE:
<223> OTHER INFORMATION: CXCR3_EXON2 TALEN TARGET

<400> SEQUENCE: 6
ttggctctgg cctctgcaaa gtggcaggtg ccctcttcaa catca            45

<210> SEQ ID NO 7
<211> LENGTH: 45
<212> TYPE: DNA
<213> ORGANISM: homo sapiens
<220> FEATURE:
<223> OTHER INFORMATION: CXCR3_EXON2b TALEN TARGET

<400> SEQUENCE: 7
tggcctgcat cagctttgac cgctacctga acatagttca tgcca            45

<210> SEQ ID NO 8
<211> LENGTH: 49
<212> TYPE: DNA
<213> ORGANISM: homo sapiens
<220> FEATURE:
<223> OTHER INFORMATION: CCDC38_EXON2 TALEN TARGET

<400> SEQUENCE: 8
ttaacaggta aagtaaaaga tggctcaacc aaagaggaca ggccttata        49

<210> SEQ ID NO 9
<211> LENGTH: 44
<212> TYPE: DNA
<213> ORGANISM: homo sapiens
<220> FEATURE:
<223> OTHER INFORMATION: CCDC38_EXON3 TALEN TARGET

<400> SEQUENCE: 9
tctaccagaa aactactttt tcatccagaa tgaagagtca ttca             44

<210> SEQ ID NO 10
<211> LENGTH: 44
<212> TYPE: DNA
<213> ORGANISM: homo sapiens
<220> FEATURE:
<223> OTHER INFORMATION: NFU1_EXON2 TALEN TARGET

<400> SEQUENCE: 10
tgcaggttct gtcatatgtt gaagaatcca tacaccatta agaa             44

<210> SEQ ID NO 11
<211> LENGTH: 44
<212> TYPE: DNA
<213> ORGANISM: homo sapiens
<220> FEATURE:
<223> OTHER INFORMATION: NFU1_EXON2 TALEN TARGET

<400> SEQUENCE: 11
tacaaagacc acttttccca ctacctgcag cctttttatca ccca            44

<210> SEQ ID NO 12
<211> LENGTH: 49
<212> TYPE: DNA
<213> ORGANISM: homo sapiens
<220> FEATURE:
<223> OTHER INFORMATION: CACGN5_EXON2 TALEN TARGET

<400> SEQUENCE: 12
ttcttgtctc cacaggtgag gagcgggggc gttgcttcac catagaata        49
```

<210> SEQ ID NO 13
<211> LENGTH: 44
<212> TYPE: DNA
<213> ORGANISM: homo sapiens
<220> FEATURE:
<223> OTHER INFORMATION: CACGN5_EXON3 TALEN TARGET

<400> SEQUENCE: 13
ttaattagag atgatccgct cagccacacc attccctctg gtca          44

<210> SEQ ID NO 14
<211> LENGTH: 44
<212> TYPE: DNA
<213> ORGANISM: homo sapiens
<220> FEATURE:
<223> OTHER INFORMATION: GGH_EXON2 TALEN TARGET

<400> SEQUENCE: 14
tgtaaagtac ttggagtctg caggtgcgag agttgtacca gtaa          44

<210> SEQ ID NO 15
<211> LENGTH: 46
<212> TYPE: DNA
<213> ORGANISM: homo sapiens
<220> FEATURE:
<223> OTHER INFORMATION: GGH_EXON3 TALEN TARGET

<400> SEQUENCE: 15
ttacagagaa agactatgaa atactttca aatctattaa tgggta          46

<210> SEQ ID NO 16
<211> LENGTH: 45
<212> TYPE: DNA
<213> ORGANISM: homo sapiens
<220> FEATURE:
<223> OTHER INFORMATION: PARP14_Exon1 TALEN TARGET

<400> SEQUENCE: 16
tgagttggta tggcaaggaa aaggaacatt caagttaact gtcca          45

<210> SEQ ID NO 17
<211> LENGTH: 45
<212> TYPE: DNA
<213> ORGANISM: homo sapiens
<220> FEATURE:
<223> OTHER INFORMATION: PARP14_Exon3 TALEN TARGET

<400> SEQUENCE: 17
ttggatacaa aactccctct tgatggtgga ttagacaaaa tggaa          45

<210> SEQ ID NO 18
<211> LENGTH: 45
<212> TYPE: DNA
<213> ORGANISM: homo sapiens
<220> FEATURE:
<223> OTHER INFORMATION: URG4_Exon_2 TALEN TARGET

<400> SEQUENCE: 18
tccatagatg gtacaaatga ggctcaggac aatgattttc caaca          45

<210> SEQ ID NO 19
<211> LENGTH: 49
<212> TYPE: DNA
<213> ORGANISM: homo sapiens
<220> FEATURE:
<223> OTHER INFORMATION: URG4_Exon_3 TALEN TARGET

```
<400> SEQUENCE: 19
tgtcactttt gggcctagag acgtaccagg tccagaaact cagcctcca          49

<210> SEQ ID NO 20
<211> LENGTH: 48
<212> TYPE: DNA
<213> ORGANISM: homo sapiens
<220> FEATURE:
<223> OTHER INFORMATION: NR1h2_Exon_2 TALEN TARGET

<400> SEQUENCE: 20
ttccaggaaa tggccccct cagcctggcg cccttcttc ttcaccca             48

<210> SEQ ID NO 21
<211> LENGTH: 49
<212> TYPE: DNA
<213> ORGANISM: homo sapiens
<220> FEATURE:
<223> OTHER INFORMATION: AMPD3_Exon_1 TALEN TARGET

<400> SEQUENCE: 21
tgaagtggat gagcaagtcc ggctcctggc ggagaaggtg tttgctaaa          49

<210> SEQ ID NO 22
<211> LENGTH: 45
<212> TYPE: DNA
<213> ORGANISM: homo sapiens
<220> FEATURE:
<223> OTHER INFORMATION: AMPD3_Exon_2 TALEN TARGET

<400> SEQUENCE: 22
tggtcactgg agccacttcc ctgcccacgc cagcaccta tgcca               45

<210> SEQ ID NO 23
<211> LENGTH: 45
<212> TYPE: DNA
<213> ORGANISM: homo sapiens
<220> FEATURE:
<223> OTHER INFORMATION: AMPD3_Exon_3 TALEN TARGET

<400> SEQUENCE: 23
ttggaggact atgagcaggc agccaagagt ctggccaagg ccta               45
```